(12) United States Patent
Hashimoto et al.

(10) Patent No.: US 6,640,634 B2
(45) Date of Patent: Nov. 4, 2003

(54) ULTRASONIC PROBE, METHOD OF MANUFACTURING THE SAME AND ULTRASONIC DIAGNOSIS APPARATUS

(75) Inventors: Shinichi Hashimoto, Yaita (JP); Satoru Tezuka, Nasu-gun (JP); Yohachi Yamashita, Yokohama (JP); Kazuhiro Itsumi, Kawasaki (JP); Tsuyoshi Kobayashi, Kawasaki (JP); Shiro Saito, Kawasaki (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 156 days.

(21) Appl. No.: 09/820,886

(22) Filed: Mar. 30, 2001

(65) Prior Publication Data

US 2002/0073781 A1 Jun. 20, 2002

(30) Foreign Application Priority Data

Mar. 31, 2000 (JP) .................................. 2000-159179
Apr. 19, 2000 (JP) .................................. 2000-118572

(51) Int. Cl.$^7$ .............................................. G01N 29/00
(52) U.S. Cl. ...................... 73/632; 73/628; 73/862.046; 600/459
(58) Field of Search .................. 73/632, 628, 579, 73/862.41, 862.046; 600/447, 443, 437, 459; 310/360, 334, 335, 337

(56) References Cited

U.S. PATENT DOCUMENTS

| | | | | |
|---|---|---|---|---|
| 3,952,387 A | * | 4/1976 | Iinuma et al. ............. | 29/25.35 |
| 4,616,152 A | * | 10/1986 | Saito et al. ................. | 310/334 |
| 4,801,835 A | * | 1/1989 | Nakaya et al. ............. | 310/358 |
| 4,894,895 A | * | 1/1990 | Rokurohta et al. ........ | 29/25.35 |
| 4,962,332 A | * | 10/1990 | Rokurohta et al. ......... | 310/335 |
| 5,434,827 A | * | 7/1995 | Bolorforosh ................ | 367/140 |
| 5,435,313 A | * | 7/1995 | Noda et al. ................. | 600/459 |
| 6,193,659 B1 | * | 2/2001 | Ramamurthy et al. ...... | 600/443 |
| 6,213,951 B1 | * | 4/2001 | Krishnan et al. ........... | 600/458 |
| 6,221,018 B1 | * | 4/2001 | Ramamurthy et al. ...... | 600/443 |
| 6,251,074 B1 | * | 6/2001 | Averkiou et al. ........... | 600/447 |
| 6,425,869 B1 | * | 7/2002 | Rafter et al. ................ | 600/458 |
| 6,465,937 B1 | * | 10/2002 | Chen et al. ................. | 310/360 |
| 6,483,228 B2 | * | 11/2002 | Hashimoto .................. | 310/334 |

FOREIGN PATENT DOCUMENTS

| | | |
|---|---|---|
| JP | 59-152800 | 8/1984 |
| JP | 7-170600 | 7/1995 |
| JP | 11-234797 | 8/1999 |
| JP | 2000-138400 | 5/2000 |

* cited by examiner

Primary Examiner—Helen Kwok
Assistant Examiner—Jacques Saint-Surin
(74) Attorney, Agent, or Firm—Oblon, Spivak, McClelland, Maier & Neustadt, P.C.

(57) ABSTRACT

A two-dimensional array ultrasonic probe comprises printed circuit boards, each carrying piezoelectric vibrators arranged in the form of a matrix and adapted to draw signal leads and grounding wires from the vibrators through the gaps separating the columns of the matrix. A row of vibrators are arranged in an array on each of the printed circuit boards and then the printed circuit boards carrying vibrators are arranged in the column to produce a two-dimensional array transducer.

24 Claims, 12 Drawing Sheets

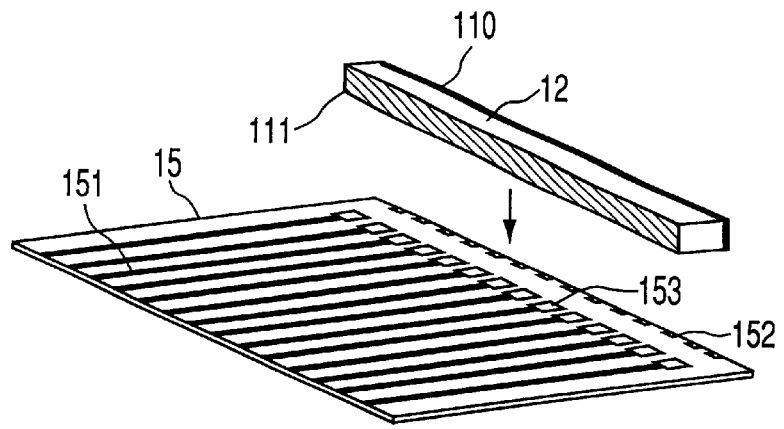
F I G. 4A
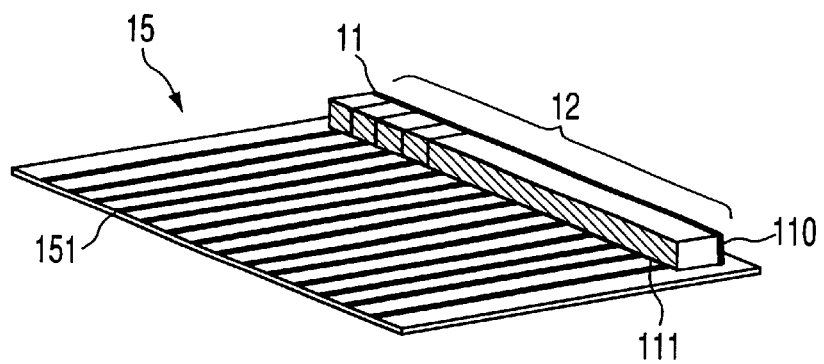
F I G. 4B
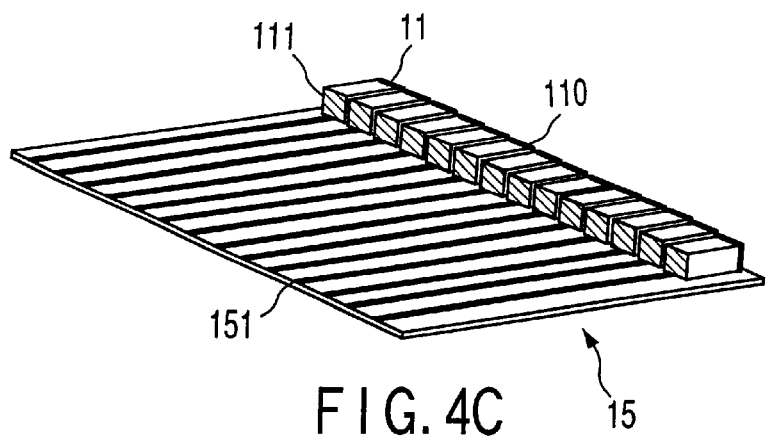
F I G. 4C

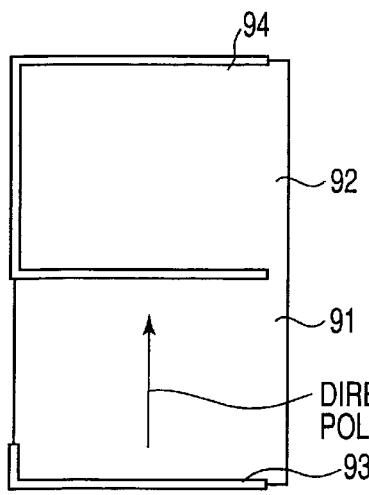
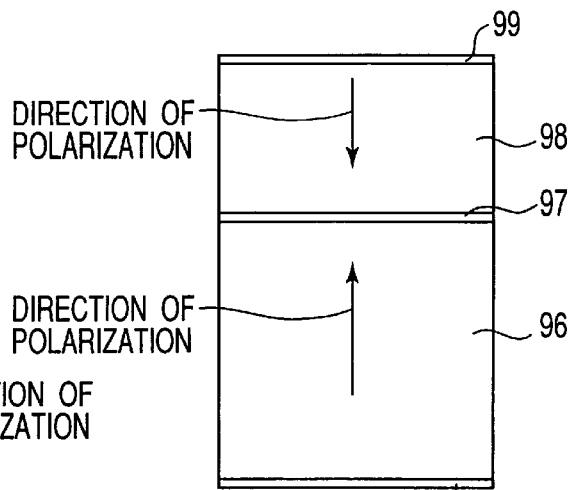
FIG. 14A  FIG. 14B
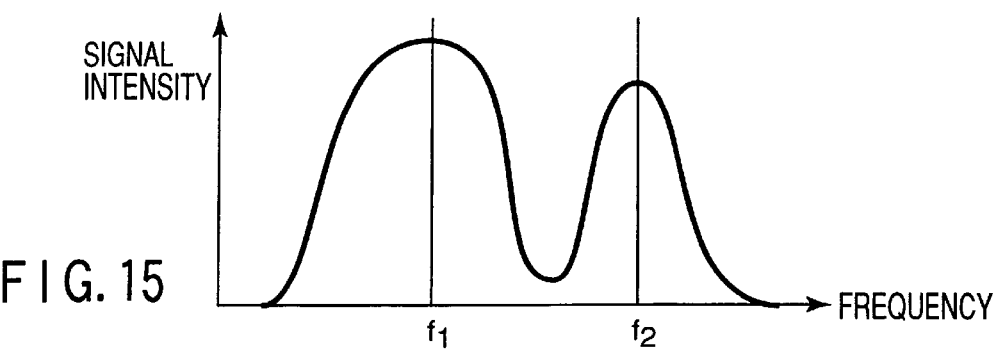
FIG. 15
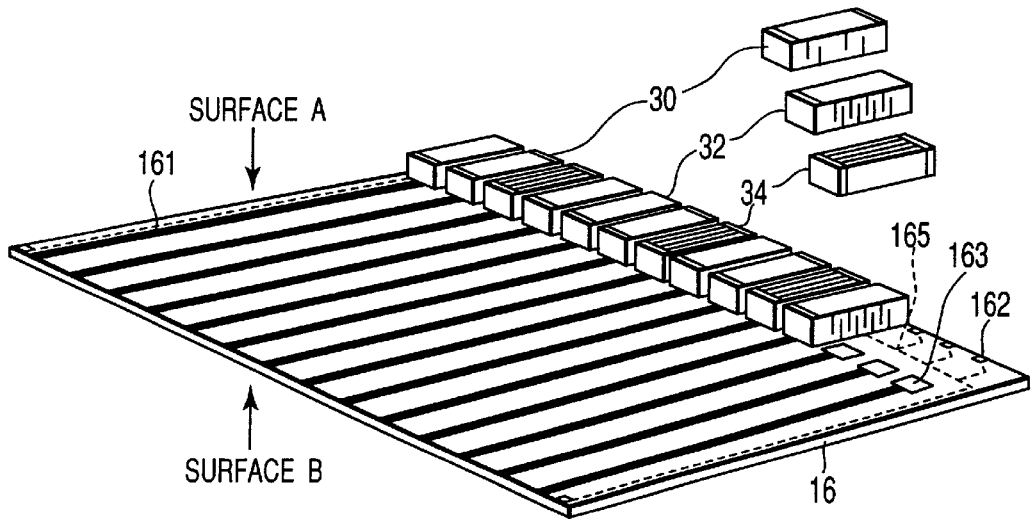
FIG. 16

ULTRASONIC PROBE, METHOD OF MANUFACTURING THE SAME AND ULTRASONIC DIAGNOSIS APPARATUS

This application is based upon and claims the benefit of priority from the prior Japanese Patent Applications No. 2000-159179 filed Mar. 31, 2000 and No. 2000-118572 filed Apr. 9, 2000, the entire contents of which are incorporated herein by reference.

BACKGROUND OF THE INVENTION

This invention relates to an ultrasonic probe to be used for ultrasonic diagnosis and ultrasonic flaw detection, a method of manufacturing such a probe and an ultrasonic diagnosis apparatus comprising such a probe.

Conventional ultrasonic probes utilized for ultrasonic diagnosis apparatus comprise a one-dimensional array probe formed by arranging short strip-shaped (narrow box-shaped) piezoelectric vibrators in an array. This is because a technique referred to as an electronic scanning method is generally used for ultrasonic scanning operations for good reasons. With the electronic scanning method, the ultrasonic vibrators of the array are provided with respective delay times when focussing the pulse to be transmitted or the received signal. Since this method allows high speed scanning and high speed alteration of the focal point of the ultrasonic beam to be transmitted or the received ultrasonic beam, it is in the main stream of ultrasonic scanning.

With the above electronic scanning method, in the case of a one-dimensional array probe, the operation of electronic focussing can be conducted on an ultrasonic wave in the direction of arrangement of the piezoelectric vibrators and an ultrasonic beam can be used for scanning. However, only an acoustic lens can be used for focussing in a direction perpendicular to the direction of arrangement (and hence to the surface to be scanned by the ultrasonic wave. This means that it is not possible to dynamically change the focal point. Additionally, any scanning operation using an ultrasonic beam cannot be conducted two-dimensionally (on a plane) because piezoelectric vibrators are arranged only one-dimensionally in conventional ultrasonic probes.

In recent years, efforts have been made to develop systems for three-dimensionally collecting and displaying ultrasonic images by arranging vibrators (ultrasonic vibrators) in the form of a matrix, dynamically focussing the ultrasonic beam in all directions and using the ultrasonic beam for three-dimensional scanning.

For such a system to be realized, it is necessary to use a two-dimensional array ultrasonic probe comprising two-dimensionally arranged vibrators. In other words, the use of a two-dimensional array ultrasonic probe is a prerequisite for realizing omnidirectional focussing and high speed three-dimensional scanning of ultrasonic waves.

Generally, in two-dimensional array probes, vibrators are arranged in the form of a matrix of m rows and n columns. In order to realize three-dimensional dynamic focussing and three-dimensional beam scanning to a satisfactory extent, a number greater than 50 have to be selected for m and also for n and vibrators have to be arranged at a micro-pitch of less than 0.5 mm. Then, more than 2,000 channels of wires have to be led out of an area of about 2 cm square.

Meanwhile, a number of proposals have been made for realizing two-dimensional array probes particularly in terms of process and configuration. For example, Japanese Patent Application KOKAI Publication No. 59-152800 discloses a method of manufacturing a two-dimensional array probe, which will be summarily described below.

Firstly, a grounding plate and a flexible printed circuit board (FPC) are connected respectively to the front and rear surfaces of a raw piezoelectric vibrator and a backing member and an acoustic adjustment layer are formed as in the case of a one-dimensional array probe. Then, the grounding plate and the FPC are bent in an appropriate manner. Subsequently, the vibrator is diced to produce array vibrators and signal leads and grounding wires are led out from the respective lateral sides of the vibrators to produce a one-dimensional array transducer. A two-dimensional array ultrasonic probe is produced by bonding a plurality of such one-dimensional array transducers.

Japanese Patent Application KOKAI Publication No. 2000-138400 discloses an ultrasonic probe comprising layer-built electronic components, including layer-built piezoelectric elements and a flexible printed circuit board bonded to the layer-built piezoelectric elements. In this ultrasonic probe, every other electrode is selected in the layer direction of the piezoelectric elements and the selected electrodes are electrically connected together by means of an electrode pattern of the flexible printed circuit board to form a first group of electrodes, while the remaining electrodes are connected together to form a second group of electrodes. An end of the electrode pattern of the flexible printed circuit board is used as the electrode section for external connection that is also electrically connected to the two groups of electrodes.

Besides the above probes, many other two-dimensional array ultrasonic probes have been proposed and include those obtained by two-dimensionally arranging electrode drawing out terminals in the form of a matrix, drawing out leads therefrom, connecting a piezoelectric vibrator plate onto a substrate and dividing the piezoelectric vibrator plate into matrix in such a way that each vibrator is found on an electrode drawing out terminal.

However, with any of the known methods, it is difficult to realize a two-dimensional array probe comprising a large number of vibrators that are arranged at a micro-pitch with a high productivity and low cost.

Meanwhile, PZT (lead zirconate-titanate) type piezoelectric ceramic materials and lead relaxa-titanate type piezoelectric monocrystalline materials are used as ultrasonic wave receiving materials in the field of medical ultrasonic diagnosis apparatus and non-destructive testing apparatus.

Additionally, as pointed out above, efforts have been made to develop two-dimensional probes comprising two-dimensionally arranged rod-shaped vibrators. By using rod-shaped vibrators, it is possible to use k33 corresponding to the longitudinal vibration of a rod for the vibration mode. The value of k33 is found between 60 and 80% in the case of PZT type ceramic materials and 80 and 94% in the case of relaxa-titanium type monocrystalline materials. These values are promising for realizing high sensitivity probes.

The technology of THI (Tissue Harmonic Imaging) is currently used to capture minute blood flow in the field of ultrasonic diagnosis apparatus. With the technology of THI, higher harmonics of the second degree of the transmitted ultrasonic wave (echo) are received and detected. Therefore, conventional ultrasonic probes realized by adopting the THI technology are forced to use the resonance frequency of the piezoelectric vibrators either for wave transmission or for wave reception or compromise the requirement of transmission and that of reception at the cost of sacrificing the frequency characteristics of the piezoelectric vibrators to a certain extent. As a result, problems arise including an undesired high drive voltage transmitted from the drive circuit and/or a reduced reception sensitivity.

Japanese Patent Application KOKAI Publication No. 11-234797 discloses a technology of using different sets of piezoelectric vibrators for ultrasonic wave transmission and reception. According to the patent document, piezoelectric vibrators are arranged in a single layer as reception vibrators while transmission vibrators are arranged to form a thin multilayer structure to raise the intensity of the transmitted ultrasonic wave. However, any two arrangements of piezoelectric vibrators of the same piezoelectric material formed at the same thickness show a substantially similar center frequency in the operating frequency band. Therefore, the use of the technology of Japanese Patent Application KOKAI Publication No. 11-234797 for THI does not significantly improve the reception sensitivity.

The above problems are particularly serious in two-dimensional array probes because down-sized vibrators are used there to make each vibrator show a reduced transmission/reception capacity.

On the other hand, in conventional two-dimensional array probes, a single piezoelectric vibrator is divided to form a two-dimensional array typically in the manner as described in Japanese Patent Application KOKAI Publication No. 7-170600.

With the technique disclosed in the above patent document, however, newly manufactured ultrasonic probes that mostly contain good vibrators can become faulty if they have even a few defective vibrators, brought about by electrodes peeling off when the single piezoelectric vibrator is cut. Therefore, a high manufacturing yield cannot be expected with the technique.

Japanese Patent Application KOKAI Publication No. 11-234797 discloses technique of uniformly rearranging the produced vibrators with reduced intervals. However, such a rearranging operation requires an extremely high level of precision.

Thus, conventional ultrasonic diagnosis apparatus employing the technology of THI are accompanied by the need of using an undesired high drive voltage transmitted from the drive circuit and/or the problem of a reduced reception sensitivity.

On the other hand, manufacturing two-dimensional arrays requires an extremely high level of precision and hence cannot be expected to provide a high manufacturing efficiency.

BRIEF SUMMARY OF THE INVENTION

In view of the above circumstances, it is therefore an object of the present invention to provide a two-dimensional array ultrasonic probe that can be manufactured easily and efficiently and operates with a high sensitivity and low inter-vibrator cross talk, a method of manufacturing such a probe and an ultrasonic diagnosis apparatus comprising such a probe.

Another object of the present invention is to provide an ultrasonic probe adapted to THI technology that can suitably be used for ultrasonic diagnostic operations using THI technology to realize low power consumption and high sensitivity, a method of manufacturing such an ultrasonic probe in a simple way and an ultrasonic diagnosis apparatus comprising such a probe.

In a first aspect of the invention, the above objects are achieved by providing an ultrasonic probe comprising a plurality of piezoelectric vibrators, a plurality of substrates having a plurality of signal lines on one of the surfaces thereof, the plurality of piezoelectric vibrators being arranged to form an array and one of the vibrator connected respectively to one of the signal lines, the plurality of substrates being arranged at predetermined intervals so that the plurality of piezoelectric vibrators is arranged in matrix arrangement, and a holding means for rigidly holding the plurality of substrates.

Thus in the first aspect of the invention, it is possible to provide a two-dimensional ultrasonic probe wherein printed circuit boards are arranged in the respective gaps separating the two-dimensionally arranged piezoelectric vibrators so as to draw electric wires therefrom for connection with the signal electrodes and the electrode connectors at lateral sides of the vibrators are connected respectively to the corresponding electric connectors on the printed circuit boards so that the signal lines from the signal electrodes of the piezoelectric vibrators can be taken out on a column by column basis.

In a second aspect of the present invention, there is provided an ultrasonic probe comprising a plurality of first vibrators adapted to transmit a first ultrasonic wave in a first frequency band to an object of examination and a plurality of second vibrators adapted to receive the reflected waves from the object of examination produced on the basis of the first ultrasonic wave in a second frequency band, the plurality of first vibrators and the plurality of second vibrators being arranged in the form of a matrix to produce an ultrasonic wave irradiation surface, the center frequency of the second frequency band being higher than the center frequency of the first frequency band.

Differently stated, two groups of vibrators with different resonance frequencies are used respectively as vibrators for transmitting an ultrasonic wave and those for receiving an ultrasonic wave in an ultrasonic probe. With this arrangement, an ultrasonic wave having a frequency different from that of the transmitted ultrasonic wave can be detected with a high sensitivity.

Generally, with THI technology adapted to receive the higher harmonics of the second degree of echo of an ultrasonic wave, it is desirable that the resonance frequency of the wave receiving vibrators is higher than that of the wave transmitting vibrators. To be more specific, the resonance frequency of the wave receiving vibrators is higher than that of the wave transmitting vibrators preferably by 1.5 to 3 times, more preferably by about two times.

Therefore, in the second aspect of the invention, an ultrasonic probe according to the invention can show an improved sensitivity for receiving an ultrasonic wave and a reduced drive voltage for transmitting an ultrasonic wave.

In a third aspect of the invention, there is provided an ultrasonic diagnosis apparatus comprising an ultrasonic probe having a plurality of first vibrators adapted to transmit a first ultrasonic wave in a first frequency band to an object of examination and a plurality of second vibrators adapted to receive the reflected waves from the object of examination produced on the basis of the first ultrasonic wave in a second frequency band, a drive circuit for driving the first vibrators with a signal having a predetermined frequency and a detection circuit for detecting the reception signal received by the second vibrators and taking out the higher harmonics of the second degree of the signal having the predetermined frequency.

Thus, an ultrasonic diagnosis apparatus in accordance with the third aspect of the invention can show an enhanced level of reception sensitivity and operates with a reduced drive voltage for transmitting an ultrasonic wave.

In a fourth aspect of the invention, there is provided an ultrasonic diagnosis apparatus comprising an ultrasonic probe having a plurality of piezoelectric vibrators including a plurality of first vibrators adapted to transmit a first ultrasonic wave in a first frequency band to an object of examination and a plurality of second vibrators adapted to receive the reflected waves from the object of examination produced on the basis of the first ultrasonic wave in a second frequency band, a plurality of substrates carrying a plurality of signal lines on one of the opposite surfaces thereof, the plurality of piezoelectric vibrators being arranged to form a matrix and connected respectively to the signal lines on a one to one basis, the plurality of substrates being arranged at predetermined intervals so as to adapt themselves to the matrix arrangement of the plurality of piezoelectric vibrators, and a securing means for rigidly securing the plurality of substrates, a drive circuit for driving the first vibrators with a signal having a predetermined frequency and a detection circuit for detecting the reception signal received by the second vibrators and taking out the higher harmonics of the second degree of the signal having the predetermined frequency.

Thus, an ultrasonic diagnosis apparatus in accordance with the fourth aspect of the invention can show an enhanced level of reception sensitivity and operates with a reduced drive voltage for transmitting an ultrasonic wave.

In a fifth aspect of the invention, there is provided a method of manufacturing an ultrasonic probe comprising a step of electrically connecting the electrodes of a plurality of layer-built piezoelectric vibrators respectively to corresponding signal lines arranged at a predetermined pitch on one of the surfaces of a plurality of substrates and mounting the layer-built piezoelectric vibrators with the lateral surfaces thereof held in contact with the respective substrates and a step of forming an ultrasonic wave transmitting surface carrying thereon the layer-built vibrators arranged two-dimensionally by arranging the plurality of substrate with the plurality of layer-built vibrators mounted thereon.

With the method of manufacturing an ultrasonic probe in accordance with the fifth aspect of the invention, it is now possible to manufacture an ultrasonic probe with a high sensitivity and low inter-vibrator cross talk relatively easily in order to realize a high manufacturing efficiency.

Additional objects and advantages of the present invention will be set forth in the description which follows, and in part will be obvious from the description, or may be learned by practice of the present invention.

The objects and advantages of the present invention may be realized and obtained by means of the instrumentalities and combinations particularly pointed out hereinafter.

BRIEF DESCRIPTION OF THE VIEWS OF THE DRAWING

The accompanying drawings, which are incorporated in and constitute a part of the specification, illustrate presently preferred embodiments of the present invention and, together with the general description given above and the detailed description of the preferred embodiments given below, serve to explain the principle of the present invention.

FIGS. 4A, 4B and 4C are schematic perspective views of a printed circuit board 15, illustrating different steps of mounting piezoelectric vibrators;

FIGS. 14A and 14B are schematic views of a 2-cycle vibrator;

FIG. 15 is a graph showing the frequency characteristics of a 2-cycle vibrator;

FIG. 16 is a schematic perspective view of a printed circuit board, illustrating a method of mounting layer-built piezoelectric vibrators for wave transmission, layer-built piezoelectric vibrators for wave reception and unused vibrators on the printed circuit board.

DETAILED DESCRIPTION OF THE INVENTION

Figure 1:
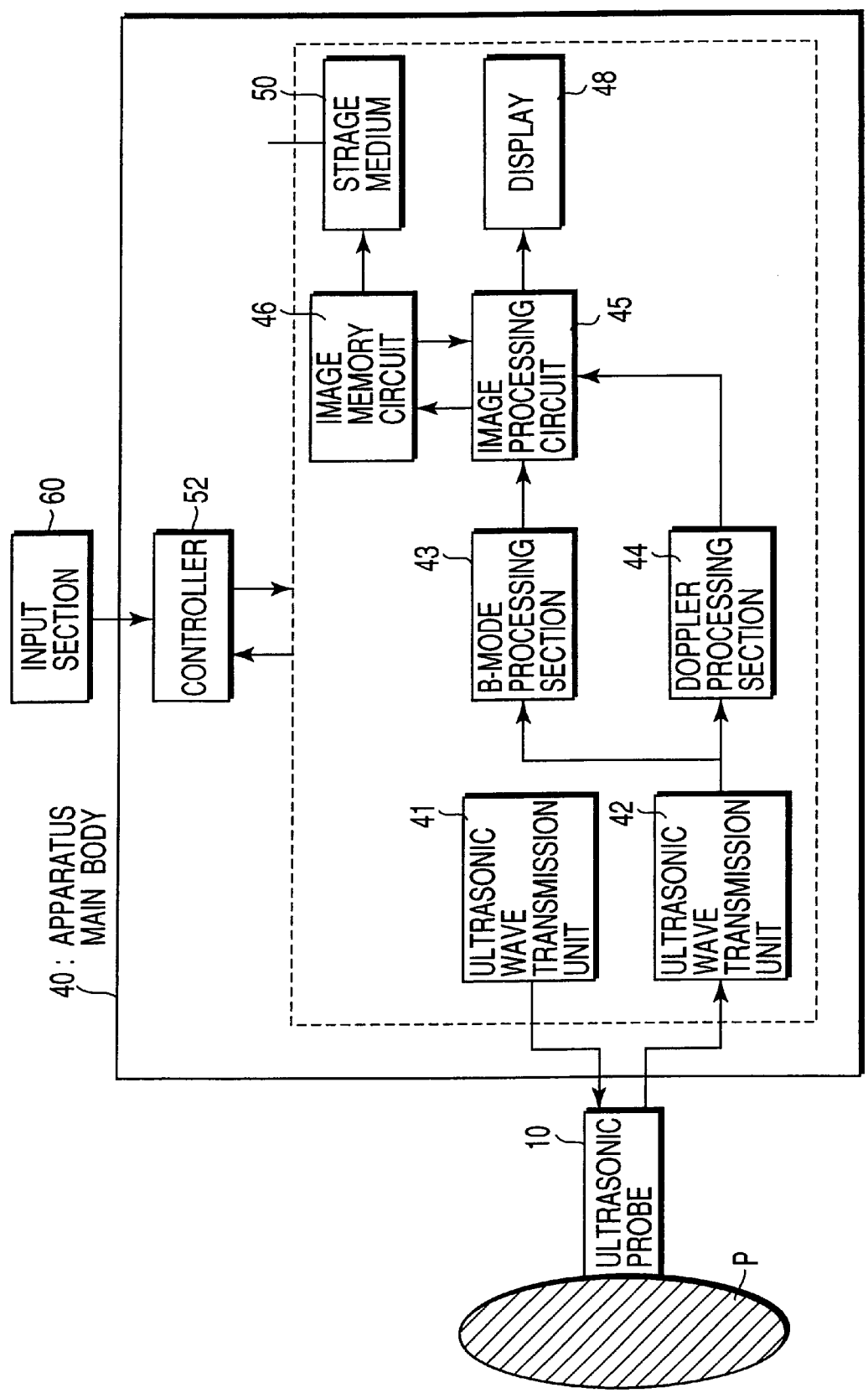
FIG. 1 is a schematic block diagram of an ultrasonic diagnosis apparatus according to the invention.

Now, the present invention will be described in greater detail by referring to the views of the drawing that illustrate first and second embodiments of the invention. Throughout the views, components that are the same or similar in terms of function and configuration are denoted by the same reference symbol and will not be described repeatedly unless necessary.

(1st Embodiment)

Firstly, the configuration of this embodiment of an ultrasonic diagnosis apparatus and ultrasonic probe will be briefly described.

FIG. 1 is a schematic block diagram of this embodiment of an ultrasonic diagnosis apparatus 1.

As shown in FIG. 1, the ultrasonic diagnosis apparatus 1 comprises an ultrasonic probe 10, an apparatus main body 40 and an input section 60.

The ultrasonic probe 10 is adapted to be brought into contact directly or by way of an acoustic coupler with an object of examination in order to transmit and receive ultrasonic wave signals. The ultrasonic probe 10 comprises piezoelectric vibrators. A probe formed by one-dimensionally arranging piezoelectric vibrators is referred to as a one-dimensional array probe while a probe formed by two-dimensionally arranging piezoelectric vibrators is referred to as two-dimensional array probe. The configuration of the ultrasonic probe 10 will be described in greater detail hereinafter.

The input section 60 is connected to the apparatus main body 40 and typically comprises buttons, a keyboard and a trackball that are used by the operator to input instructions for controlling the diagnosis apparatus and selecting parameters for defining the image quality.

The apparatus main body 40 comprises an ultrasonic wave transmission unit 41, an ultrasonic wave reception unit 42, a B mode processing circuit 43, a Doppler processing circuit 44, an image processing circuit 45, an image memory circuit 46, a display section 48, a storage medium 50 and a controller 52. The apparatus main body 40 is used to drive the ultrasonic probe 10 and processes the reception signal obtained from the object of examination by way of the ultrasonic probe 10. The above components operate in a manner as described below.

The ultrasonic transmission unit 41 includes a trigger generator, a delay circuit and a pulser circuit (not shown) and generates a convergent ultrasonic pulse by generating a pulse-shaped ultrasonic wave and transmitting it to the vibrators of the probe 10. The transmission unit 41 is provided with a switch function and adapted to instantaneously change the transmission frequency and the transmission drive voltage, according to instructions of the controller 52. Particularly, the transmission drive voltage can be instantaneously shifted by arranging a linear amplifier type transmission circuit or by electrically switching a plurality of power source units.

The ultrasonic transmission unit 41 transmits an ultrasonic wave according to a predetermined sequence of operation under the control of the controller 52.

The ultrasonic reception unit 42 receives the echo signal output from each of the vibrators of the probe 10 and scattered in the tissues of the object of examination. The received echo signals are amplified by a preamplifier arranged for each channel in the ultrasonic reception unit 42, subjected to A/D conversion, provided with a delay time necessary for determining the reception directivity by a reception delay circuit and then added by an adder. The adding operation is designed to emphasize the reflection component from the direction corresponding to the reception directivity of the reflected wave so that a comprehensive ultrasonic beam can be formed for both transmission and reception on the basis of the transmission directivity and the reception directivity obtained by the above processing operation.

With regard to the echo signal input from the ultrasonic reception unit 42, the B mode processing circuit 43 is adapted to perform an processing operation for logarithmic amplification of echo signals and envelope detection on the input echo signals in order to generate data expressing the signal intensity by brightness.

The Doppler processing circuit 44 performs frequency analysis on the speed information from the echo signals and transmits the obtained result of the analysis to the image processing circuit 45.

The image processing circuit 45 transforms the string of scanning line signals obtained by ultrasonic wave scanning into a string of scanning line signals in a standard video format. Additionally, the image processing circuit 45 displays video signals synthetically produced from character information on selected various parameters and scales on the display section 48. As a result, a tomographic image showing the profile of the probed tissues of the object of examination is displayed on the display section 48. The image processing circuit 45 also generates a TIC (Time Intensity Curve) on the basis of a plurality of pieces of ultrasonic image information obtained by the ultrasonic probe.

The image memory circuit 46 comprises a storage memory for storing image data. The information stored in the image memory circuit 46 can be retrieved after the diagnosis and a moving image can be formed and displayed by using a plurality of images stored in the memory circuit.

The storage medium 50 stores a diagnosis analysis program, which will be described hereinafter. It can also be used for storing images in the image memory circuit 46.

The controller 52 operates as information processing device (computer). In other words, it is the control means for controlling the operation of the ultrasonic diagnosis apparatus main body 11. The controller 52 is adapted to change, if necessary, the conditions of transmission of the transmission unit such as the frequency and the drive voltage and combine the information on the conditions of transmission and the diagnostic image obtained under those conditions and add the obtained data to the image information or store them in the storage medium.

(Ultrasonic Probe)

Now, the configuration of the ultrasonic probe 10 will be described in detail. For the purpose of keeping the integrity of the overall description, assume that the ultrasonic probe 10 is a two-dimensional array ultrasonic probe, although the following description is equally applicable to a one-dimensional array ultrasonic probe.

Figure 2:
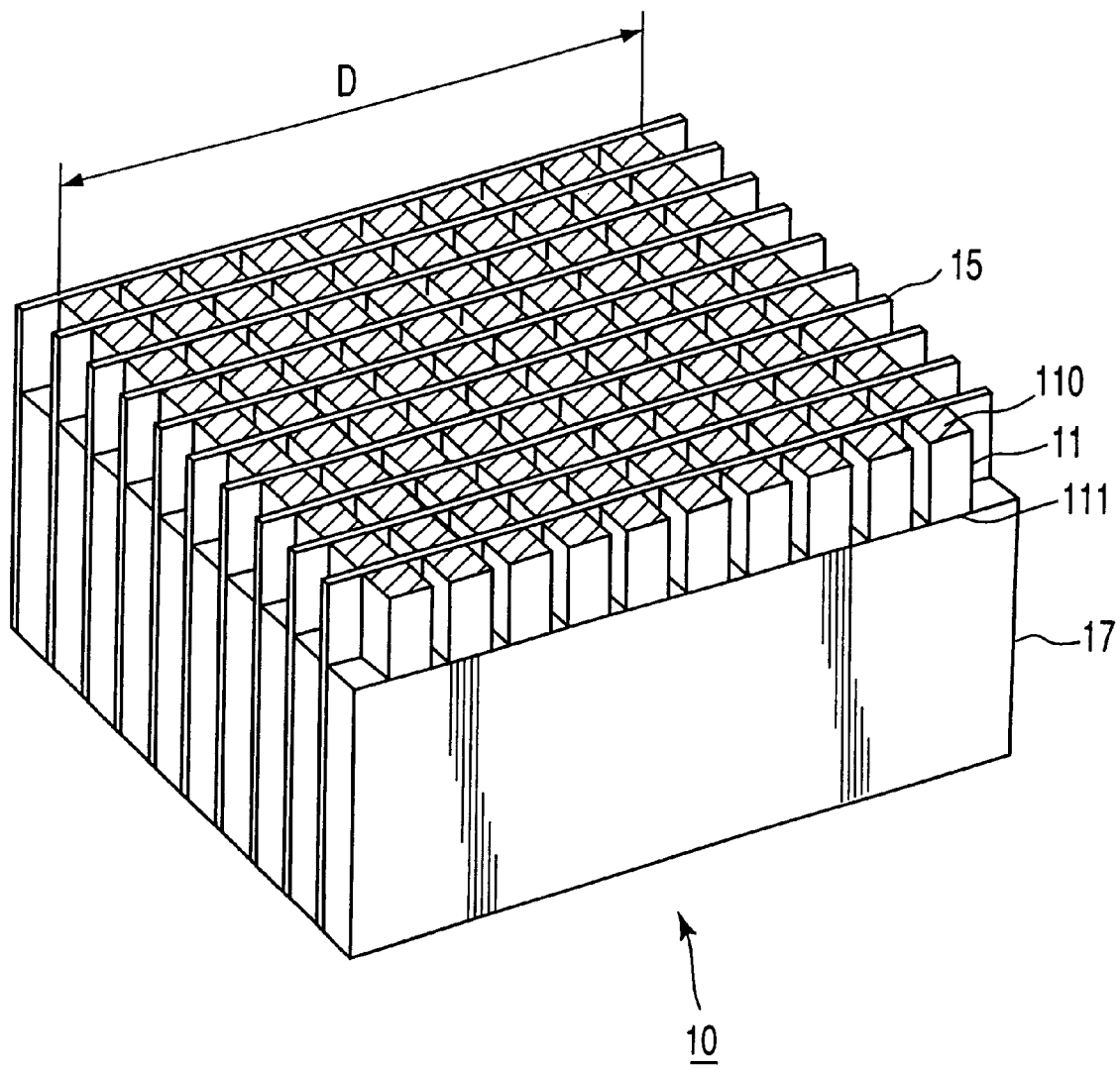
FIG. 2 is a schematic perspective view of a two-dimensional array ultrasonic probe according to the invention.

FIG. 2 is a schematic perspective view of the two-dimensional ultrasonic probe 10.

Referring to FIG. 2, the two-dimensional array ultrasonic probe 10 comprises grounding electrodes 110, signal electrodes 111 and a plurality of piezoelectric vibrators 11 arranged in the form of a matrix along with signal lines 151, ground connection pads 152 and signal connection pads 152 arranged on a side of the probe (see FIGS. 3A through 3C) as well as printed circuit boards 15 arranged in parallel with each other to fill the respective gaps separating the piezoelectric vibrators 11 and a backing member 17 pinching the printed circuit boards 15.

Piezoelectric vibrators 11 are arranged along an edge of each printed circuit board 15 at regular intervals. Each piezoelectric vibrator 11 is provided on each of the opposite sides facing respective printed circuit boards 15 with an electrode connecting section 112 to be electrically connected to one of the signal lines 151 of the corresponding printed circuit board 15 (see FIG. 3A). Each piezoelectric vibrator 11 additionally has a signal electrode 111 and a grounding electrode 110 that are thicker than comparable ordinary electrodes.

Each printed circuit board 15 to be used for leading signals is provided with signal lines 151 corresponding to the respective vibrators that are arranged two-dimensionally, signal connection pads 153 to be connected to respective signal electrodes 111 and ground connection pads 152 to be connected to respective grounding electrodes 110. Each of the signal connection pads 153 and 152 has a solder layer on some of the surfaces thereof. The ground connection pads 152 are used to hold the vibrators. The leads of the grounding electrodes 110 to be used for the purpose of grounding will be described hereinafter.

The backing member 17 is arranged along the backs of the corresponding piezoelectric vibrators 11 to mechanically support the piezoelectric vibrators 11. The backing member 17 operates to brake the piezoelectric vibrators 11 in order to curtail the ultrasonic pulse. The backing member 17 is made to be sufficiently thick show a thickness sufficiently large relative to the wavelength of the ultrasonic wave to be used for the probe in order to make the transducers operate with good acoustic characteristics (and satisfactorily attenuate the ultrasonic wave).

(Method of Manufacturing Ultrasonic Probe 10)

Now, a method of manufacturing a two-dimensional array ultrasonic probe 10 will be described.

Referring to the drawing, this manufacturing method comprises a step of mounting a plurality of piezoelectric vibrators 11 on each printed circuit board 15, a step of arranging a plurality of printed circuit boards 15 at a predetermined pitch to produce a group of piezoelectric vibrators arranged in the form of a matrix and a step of forming lead wires of the grounding electrodes and an acoustic adjustment layer. Each of the steps will be discussed in detail below. Note that the backing member 17 is provided in the step of forming a two-dimensional ultrasonic wave irradiation surface.

(1) Mounting Piezoelectric Vibrators 11 on a Printed Circuit Board 15

Figure 3A:
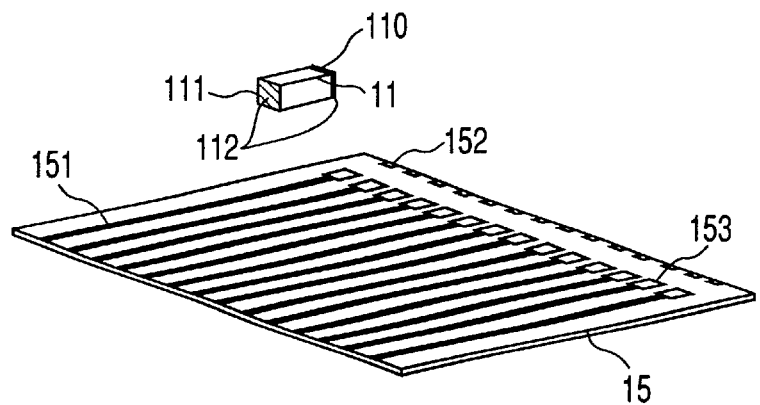
FIGS. 3A, 3B and 3C are schematic perspective views of a printed circuit board 15, illustrating different steps of mounting piezoelectric vibrators.

Firstly, pre-processed piezoelectric vibrators 11 are arranged on a printed circuit board 15 in a manner as shown in FIG. 3A. Solder paste is applied in advance to the signal connection pads 153 and the ground connection pads 152. The piezoelectric vibrators 11 are arranged in such a way that the electrode connecting sections 112 of each piezoelectric vibrator are held vis-a-vis the corresponding signal connection pad 153 and the corresponding ground connection pad 152. The electrode connecting sections 112 are provided on the lateral sides facing the printed circuit board 15 of the grounding electrode 110 and the signal electrode 111. However, the lateral side of the grounding electrode 110 and that of the signal electrode 111 facing the printed circuit board 15 per se may be used as electrode connecting sections 112 if they have a sufficient large surface area.

Figure 3B:
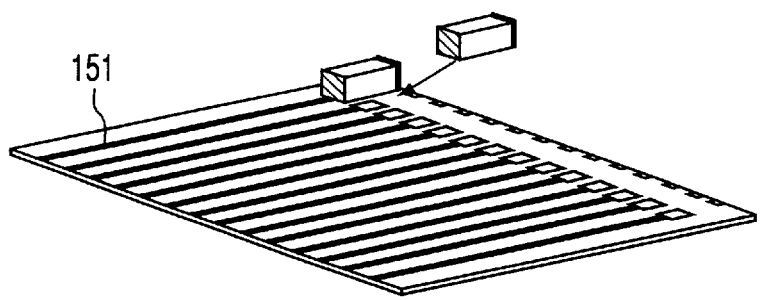
Figure 3C:
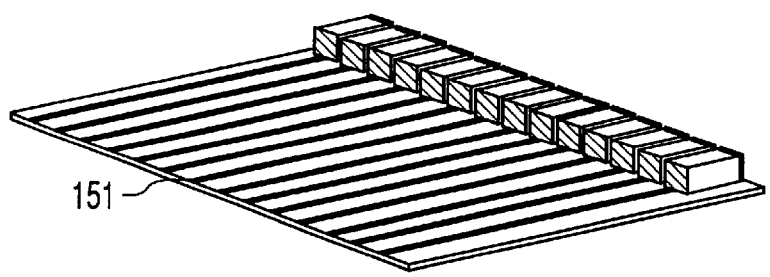

As all the piezoelectric vibrators 11 are arranged in the manner as shown in FIG. 3B to produce a printed circuit board 15 carrying piezoelectric vibrators 11 that are arranged along an edge thereof at a predetermined pitch as shown in FIG. 3C. A predetermined number of printed circuit boards 15 identical with the one shown in FIG. 3C are prepared in the same way.

Then, each printed circuit board 15 is put in a solder reflow furnace to melt the solder paste and the solder layer of each connection pad so that the grounding electrode 110 and the signal electrode 111 of each piezoelectric vibrator 11 are connected respectively to the corresponding ground connection pad 152 and the corresponding signal connection pad 153.

The above described manufacturing method provides the following advantages because of the above step.

The piezoelectric vibrators 11 have an oblong rod-shaped profile extending in the direction of vibration. Therefore, they can be mounted and secured in position as an oblong side of each of them is placed on the corresponding surface of the printed circuit board 15.

Additionally, the piezoelectric vibrators 11 are arranged in such a way that the electrode connecting sections 112 of each piezoelectric vibrator are held in a position relative to the corresponding signal connection pad 153 and the corresponding ground connection pad 152 and connected to the latter after melting the solder. This means that a self-alignment effect can be expected due to the surface tension of solder and hence the vibrators can be arranged at the same pitch as the arrangement of the connection pads.

Furthermore, piezoelectric vibrators 11 can be mounted on a printed circuit board 15 by means of general purpose techniques for mounting electronic parts of dimensions of 0.3 mm×0.3 mm×0.6 mm on a printed circuit board. With this technique, it is possible to mount not only piezoelectric vibrators of the above cited dimensions but also smaller ones.

Now, another method for mounting piezoelectric vibrators 11 on a printed circuit board 15 will be described by referring to FIGS. 4A, 4B and 4C.

Referring firstly to FIG. 4A, a plate-shaped piezoelectric vibrator 12 has a width of a two-dimensional array (equal to D in FIG. 1) is provided with a grounding electrode 110 and a signal electrode 111 as in the case of piezoelectric vibrator 11.

The plate-shaped piezoelectric vibrator 12 is arranged on a printed circuit board 15. Note that the piezoelectric vibrator 12 is arranged in such a way that the electrode connecting sections 112 of the piezoelectric vibrator are held vis-à-vis the corresponding signal connection pads 153 and the corresponding ground connection pads 152 on the printed circuit board 15 as described above. A predetermined number of printed circuit boards 15 identical with the above described one are prepared in the same way.

Then, each printed circuit board 15 is put in a solder reflow furnace to melt the solder paste and the solder layer of each connection pad so that the grounding electrode 110 and the signal electrode 111 of the piezoelectric vibrator 11 are connected respectively to the corresponding ground connection pads 152 and the corresponding signal connection pads 153.

The plate-shaped vibrator 12 that is electrically connected to the corresponding components is then divided into unit vibrators by means of a cutting machine such as a dicing saw (along cutting grooves 32 to produce individual vibrators). The signal lines 151 on the printed circuit board 15 are arranged at the same pitch as that of the arrangement of the individual vibrators so that the cutting operation is required only to cut the plate-shaped piezoelectric vibrators. With this method of cutting a plate-shaped vibrator 12 into individual unit vibrators 11, it is possible to produce a printed circuit board 15 carrying piezoelectric vibrators 11 thereon that are arranged at a predetermined pitch as shown in FIG. 4C.

In the case of FIGS. 3A through 3D and 4A through 4C, the signal electrodes 110 and the grounding electrodes 111 of the vibrators 11 and the corresponding connection pads 152, 153 on the printed circuit board are connected by means of solder. However, the present invention is by no means limited to that mode of connection and solder may be replaced by electrically conductive paste of anisotropic conductive film.

A manufacturing method having the above step can reduce the volume of operation of mounting piezoelectric vibrators 11 in addition to the above advantages and arrange piezoelectric vibrators 11 highly accurately because a single plate-shaped vibrator 12 is mounted on a printed circuit board 15 and individual unit piezoelectric vibrators 11 are produced by subsequently cutting the plate-shaped piezoelectric vibrator 12.

(2) Preparation of Groups of Vibrators Arranged in the Form of a Matrix

Now, the step of forming groups of vibrators arranged in the form of a matrix will be described by referring to FIGS. 5A and 5B.

Figure 5A:
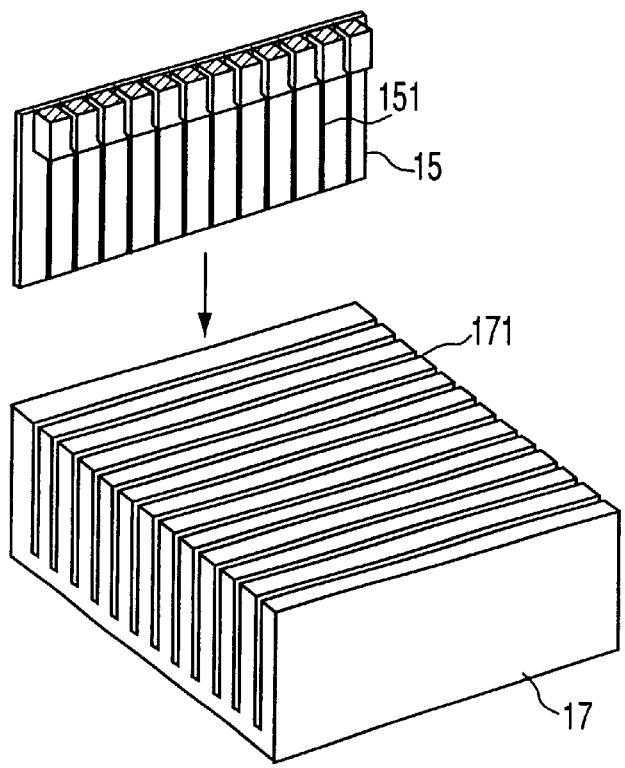
FIGS. 5A and 5B are schematic perspective views of a group of vibrators, illustrating different steps of arranging them in the form of a matrix.
Figure 5B:
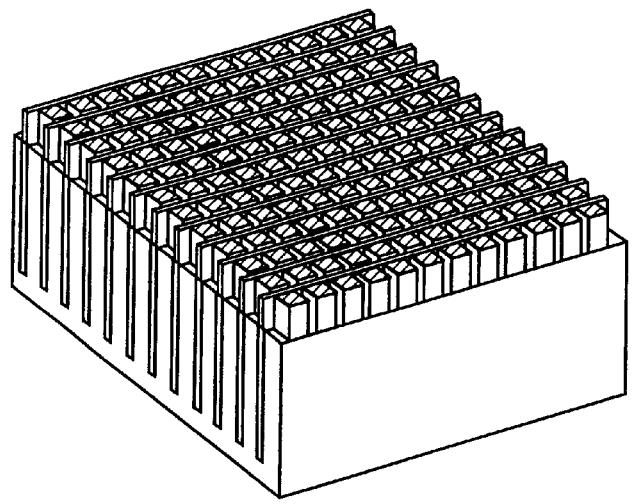

As shown in FIG. 5A, the backing member 17 is provided with a number of grooves 171 necessary for receiving respective printed circuit boards 15. A printed circuit board 15 carrying a row of vibrators is inserted into each of the grooves 171 and the bottom surfaces of the piezoelectric vibrators 11 (the sides of the signal electrodes of the piezoelectric vibrators) are bonded to the backing member 17 to produce a group of piezoelectric vibrators 11 arranged in the form of a matrix as shown in FIG. 5B.

The backing member 17 is typically made of rubber and hence can be worked with ease. Therefore, it is possible to form the grooves 171 at a desired (very small) pitch. In other words, with a manufacturing method comprising this step, it is possible to produce a group of vibrators arranged in the form of matrix if the piezoelectric vibrators arranged on the printed circuit board 15 have very small dimensions.

Now, another method that can be used for producing a group of vibrators arranged in the form of a matrix will be described by referring to FIGS. 6A, 6B and 6C.

Figure 6A:
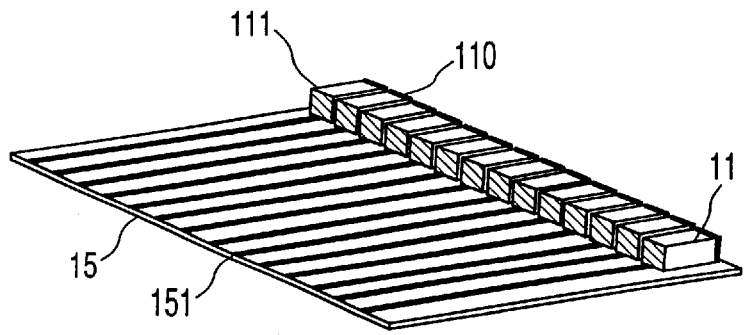
FIGS. 6A, 6B and 6C are schematic perspective views of a group of vibrators, illustrating the different steps of arranging them in the form of a matrix.
Figure 6B:
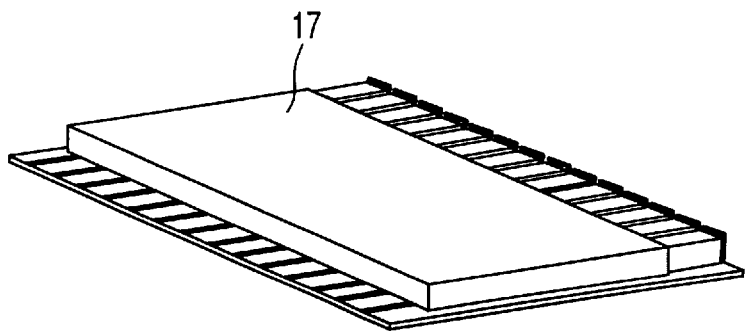

Referring firstly to FIG. 6A, a row of piezoelectric vibrators 11 are arranged on a printed circuit board 15. Then, an acoustic packing 17 is placed on the signal electrode side of the piezoelectric vibrators 11 as shown in FIG. 6B and bonded to the latter typically by means of an adhesive agent. The backing member 17 has such a thickness that the sum of the thickness of the backing member 17 and that of the printed circuit board 15 is substantially equal to the pitch of the arrangement of vibrators.

Figure 6C:
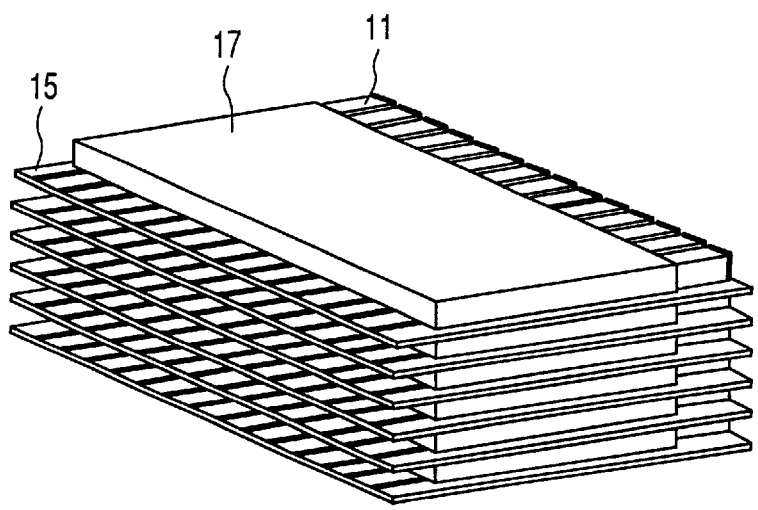

Printed circuit boards 15, each having a configuration as shown in FIG. 6C, are then laid one on the other by a number greater than the number of rows of two-dimensional array transducers as shown in FIG. 6C in such a way that the ultrasonic wave irradiating surfaces of the piezoelectric vibrators are flush with each other and the rows and the columns of the piezoelectric vibrators are aligned to form a matrix. Then, the layers are bonded together to produce a group of piezoelectric vibrators 11 arranged in the form of a matrix.

Figure 7A:
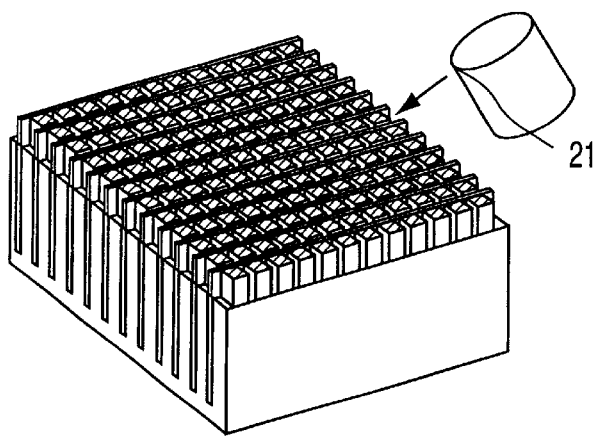
FIGS. 7A, 7B and 7C are schematic perspective views of a group of vibrators, illustrating the different steps of forming leads for grounding electrodes and an acoustic adjustment layer along with other components.
Figure 7B:
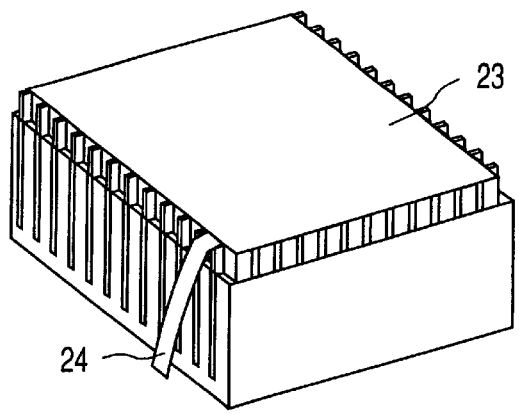
Figure 7C:
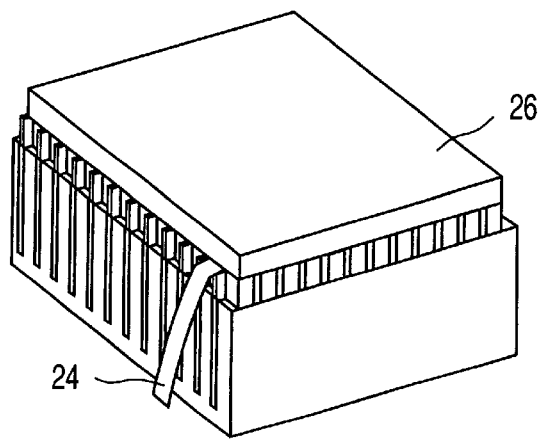

A manufacturing method having the above step makes the alignment of piezoelectric vibrators easier than the method of laying one-dimensional array structures because it is adapted to lay plate-shaped units, each comprising piezoelectric vibrators 11 and a backing (3) Formation of a Grounding Electrodes Lead Wire and an Acoustic Adjustment Layer and So On Now, the operation of forming a grounding electrode lead wire, an acoustic adjustment layer and so on by referring to FIGS. 7A, 7B, 7C will be explained.

As shown in FIG. 7A, caulking resin 21 is filled in the gaps separating the piezoelectric vibrators 11.

Subsequently, as shown in FIG. 7B, the grounding electrodes 110 of the piezoelectric vibrators 11 are exposed typically by grinding and a common electrode 23 is formed typically by evaporation or applying electrically conductive paste. Then, a lead wire 24 is formed to the common electrode 23 apart from the leads for the signal lines.

After forming the common electrode 23 and the lead 24, an acoustic adjustment layer 26 is formed on the common electrode 23 in a manner as shown in FIG. 7C. If necessary, the acoustic adjustment layer 26 may be divided for the vibrators and an acoustic lens and/or an acoustic coupling member may be formed on the acoustic adjustment layer 26.

Finally, although not shown, the back surface of the backing members are polished and/or cut to expose the end faces of the signal lines 151 of the printed circuit boards 15 and leads are drawn from the terminals.

With the above manufacturing method, a two-dimensional array probe is possible without difficulty even when it is made to have a large number of piezoelectric vibrators and the individual piezoelectric vibrators are made to have reduced dimensions because individual piezoelectric vibrators 11 are mounted on printed circuit boards 15 with signal leads drawn therefrom and the printed circuit boards 15 carrying vibrators 11 are arranged in parallel with each other to produce a two-dimensional array of piezoelectric vibrators 11. As a result, it is now possible to manufacture, at low cost, an ultrasonic probe with a high sensitivity and low inter-vibrator cross talk to realize a high manufacturing efficiency.

Alternative manufacturing methods are described above for some of the steps. It is be appreciated that a two-dimensional array ultrasonic probe 10 can be prepared by selecting any of them as so long as the combined steps of the overall manufacturing process are coherent.

Now, a modified two-dimensional array ultrasonic probe 10 will be described below.

Figure 8A:
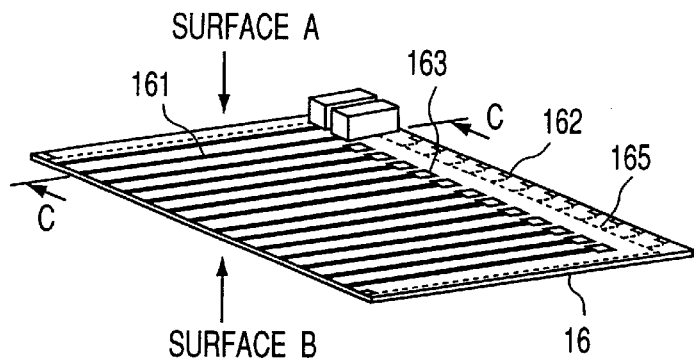
FIGS. 8A and 8B are schematic views of a printed circuit board 16, illustrating different steps of mounting piezoelectric vibrators.
Figure 8B:
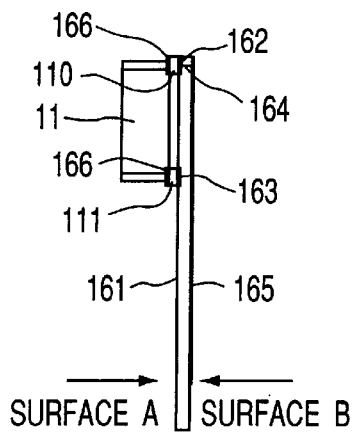

FIGS. 8A and 8B are schematic views of a modified two-dimensional array ultrasonic probe 10. FIG. 8A is a schematic perspective view of a printed circuit board 16 of the second type having an arrangement for signal leads that is different from its counterpart of the above described printed circuit board 15 and mounted with piezoelectric vibrators 11. FIG. 8B is a schematic cross sectional view taken along line C—C in FIG. 8A.

As seen from FIGS. 8A and 8B, surface A of the printed circuit board 16 of the second type carries thereon signal lines 161 that correspond to respective piezoelectric vibrators 11, signal connection pads 163 to be connected to the respective signal electrodes 111 of the piezoelectric vibrators 11 and ground connection pads 162 to be connected to the respective grounding electrodes 110 of the piezoelectric vibrators 11. The signal connection pads 163 are connected to the respective signal lines. On the other hand, surface B of the printed circuit board 16 of the second type carries thereon grounding lines 165 corresponding to the respective piezoelectric vibrators 11. The grounding lines 11 and the corresponding respective grounding electrodes on the surface A are electrically connected by way of respective through holes 164. A solder layer 166 is arranged on the surfaces of the connection pads 162, 163 for securing the piezoelectric vibrators 11 in position.

With the printed circuit board 16 of the second type having the above configuration, wires for electric signals can be led by way of the signal lines 161, while the grounding wires can be led by way of the grounding lines 165. Now, the operation of mounting a plurality of piezoelectric vibrators 11 on a printed circuit board 16 of the second type and providing them with lead wires will be described below.

Firstly, as shown in FIG. 8A, properly dimensioned piezoelectric vibrators 11 are mounted on a printed circuit board 16 and the electrodes 110, 111 are connected to the corresponding connection pads on the printed circuit board 16 to produce an array of vibrators arranged in a row. A lateral side of the printed circuit board 16 of the second type is used for connecting the grounding electrodes 110 and the signal electrodes 111 (see the leads of the electrodes 110, 111 in FIG. 8B).

As pointed out earlier, each piezoelectric vibrator 11 has a signal electrode 111 and a grounding electrode 110 that are thicker than comparable ordinary electrodes. However, if the signal electrode 111 and the grounding electrode 110 of each piezoelectric vibrator 11 cannot be satisfactorily connected only by using a lateral side of the printed circuit board 16 of the second type, an electrode connecting section may be arranged on the corresponding lateral side of the piezoelectric vibrator 11.

In this way, the printed circuit board 16 of the second type is made to carry all the piezoelectric vibrators 11 that are arranged in a row.

The subsequent steps are identical with those described above except that neither a common electrode 23 nor a lead 24 need to be formed.

Note that a two-dimensional array ultrasonic probe comprising printed circuit boards 16 of the second type can be manufactured by any of the above described methods (1), (2) and (3), although it may be needless to say that neither a common electrode 23 nor a lead 24 need to be formed.

Therefore, with a two-dimensional array ultrasonic probe formed by using printed circuit boards 16 of the second type, a signal line 161 and a grounding line 165 can be led out from each piezoelectric vibrator 11 and arranged side by side to realize an arrangement with low inter-channel cross talk.

(2nd Embodiment)

Now, the configuration of the second embodiment of the ultrasonic diagnosis apparatus and ultrasonic probe 10 will be briefly described. This embodiment of the ultrasonic probe 10 comprises piezoelectric vibrators having an impedance or frequency band adapted to ultrasonic wave transmission and those having an impedance or frequency band adapted to ultrasonic wave reception. In other words, this embodiment of an ultrasonic probe shows an improved higher harmonics receiving efficiency as a result of using separate piezoelectric vibrators for wave transmission and reception.

Figure 9:
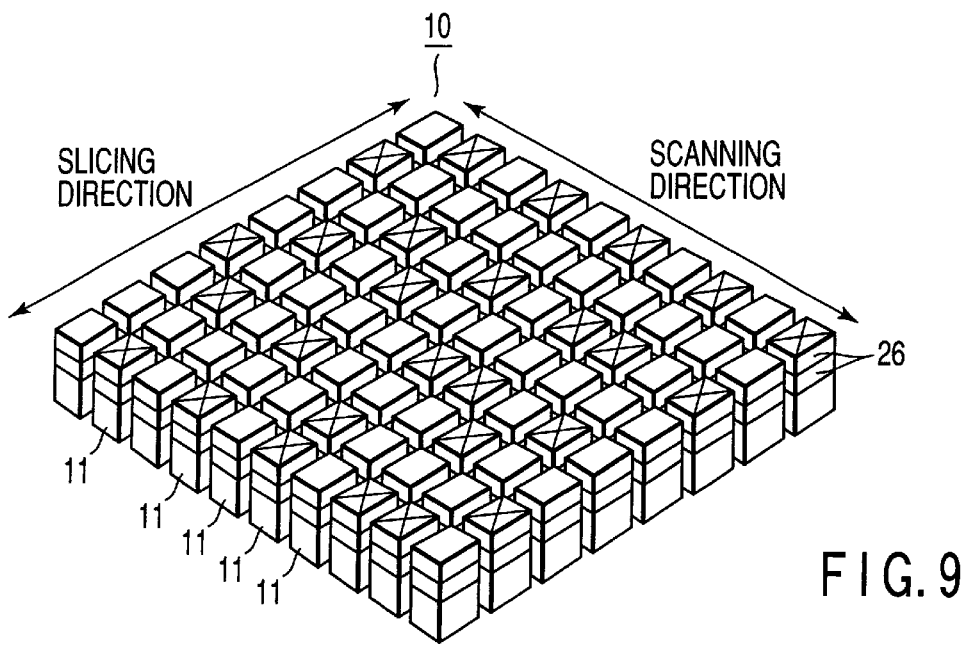
FIG. 9 is a schematic perspective view of an embodiment of ultrasonic probe 10 according to the invention.

FIG. 9 is a schematic perspective view of the embodiment of ultrasonic probe. As shown in FIG. 9, the ultrasonic probe 10 is a two-dimensional array probe realized by arranging, in the slicing direction, a plurality of one-dimensional arrays of piezoelectric vibrators 11 that are arranged in the scanning direction to form a two-dimensional ultrasonic irradiation surface. Each group of piezoelectric vibrators arranged one-dimensionally in the scanning direction for transmission are driven selectively in the same scanning line and the emitted ultrasonic wave is made to converge and scan the object of examination. Then, the piezoelectric vibrators arranged to receive the higher harmonics of the second degree out of the wave reflected by the object of examination are used to detect the condition of a part of the object of examination located at a predetermined depth. It is possible to probe the object of examination along a cross section perpendicular to the two-dimensional array by slightly displacing the focal length of the groups of piezoelectric vibrators arranged one-dimensionally in the scanning direction.

The ultrasonic probe 10 comprises a group of piezoelectric vibrators 11a for wave transmission and another group of piezoelectric vibrators 11b with different characteristics, for wave reception. The term "characteristics" as used herein include at least one of acoustic impedance, frequency band and electric impedance. The configuration of each of the piezoelectric vibrators 11a, 11b will be described in greater detail hereinafter.

Figure 10:
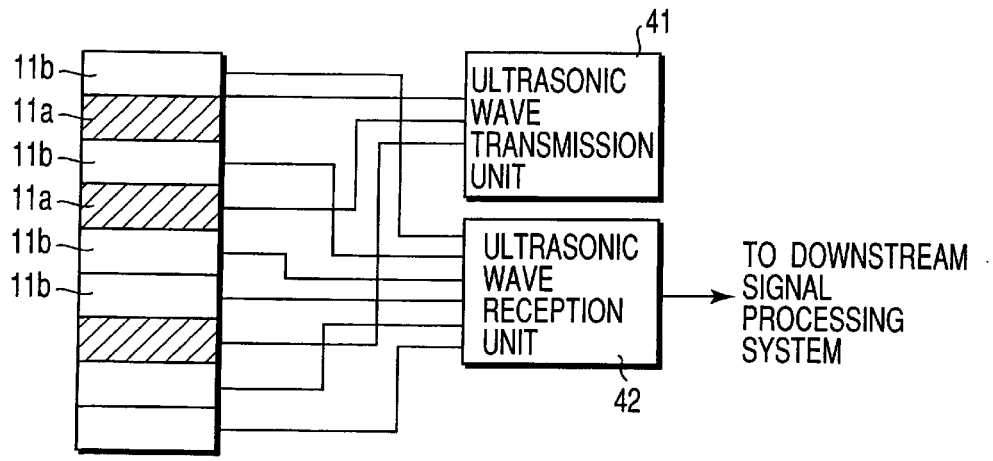
FIG. 10 is a schematic circuit diagram illustrating a mode of connecting an ultrasonic probe 10 and an ultrasonic diagnosis apparatus 1.

FIG. 10 is a schematic circuit diagram illustrating a mode of connecting an ultrasonic probe 10 and an ultrasonic diagnosis apparatus 1. Referring to FIG. 10, the ultrasonic probe 10 comprises piezoelectric vibrators 11a for wave transmission and piezoelectric vibrators 11b for wave reception that are arranged in an intermingled fashion. One of the electrodes formed on each piezoelectric vibrator 11a for wave transmission is connected to ultrasonic wave transmission unit 41 for transmitting drive signals, while the other electrode is connected to GND. The piezoelectric vibrators 11a are adapted to be driven by a drive signal of the center frequency of the vibration frequency band of the vibrators 11a to transmit an ultrasonic wave from the ultrasonic wave transmission unit 41 toward the object of examination.

On the other hand, one of the electrodes formed on each of the piezoelectric vibrators 11b for wave reception is connected to ultrasonic wave reception unit 42 for detecting reception signals, while the other electrode is connected to GND. The piezoelectric vibrators 11b are adapted to receive the wave reflected by the object of examination with the center frequency of a vibration frequency band higher than the frequency of the drive signals. The received signals are processed by the ultrasonic wave reception unit 42 and the higher harmonics of the second degree are extracted. The extracted higher harmonics of the second degree are output to the immediate downstream unit.

An acoustic adjustment layer 26 shown in FIG. 9 is formed on the ultrasonic wave receiving surface of the piezoelectric vibrators for wave reception. The acoustic adjustment layer 26 is arranged to efficiently transmit ultrasonic waves between the piezoelectric vibrators and the object of examination.

Preferably, a backing member (not shown) is arranged on the surface of the piezoelectric vibrators located opposite to the ultrasonic wave transmitting surface and the piezoelectric vibrators 11 are bonded to the backing member. The backing member is made of a material that can attenuate ultrasonic waves. Thus, the backing member attenuates the ultrasonic waves emitted from the surface opposite to the ultrasonic wave receiving surface and prevents any undesired vibrations of the piezoelectric vibrators from taking place.

Now, the configuration of the piezoelectric vibrators 11a, 11b will be described in greater detail.

Figure 11:
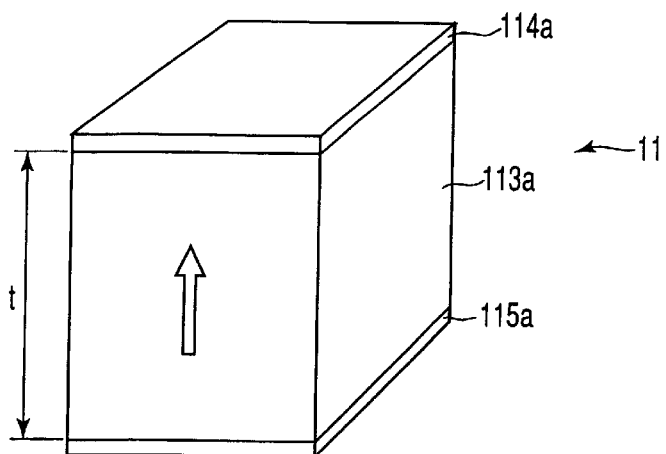
FIG. 11 is a schematic perspective view of a piezoelectric vibrator 11.

FIG. 11 is a schematic perspective view of a piezoelectric vibrator 11, which may be either for wave transmission or for wave reception.

The piezoelectric vibrator 11 comprises a piezoelectric member 113a and at least a pair of electrodes 114a, 115a arranged to apply an electric field to the piezoelectric member 113a. One of the paired electrodes, or the electrode 114a, is connected to the ultrasonic wave transmission unit 41 or the ultrasonic wave reception unit 42 and the other electrode 115a is grounded.

The piezoelectric member 113a can be formed by using a known piezoelectric material such as a PZT type piezoelectric ceramic material, a lead relaxa-titanate type monocrystalline piezoelectric material. PZT type piezoelectric ceramic materials that can be used for the purpose of the invention include a 3-compound type material formed by adding lead magnesium niobate (PMN) and lead nickel niobate (PNN) in the form of solid solution to PZT by 5 through 50 mol %. Lead relaxa-titanate type monocrystalline piezoelectric materials that can be used for the purpose of the invention include single crystal of a compound expressed by formula $Pb(B1B2)1\text{-}xTixO3$ (B1 is at least an element selected from Zn, Mg, Ni, In, Sc, Yb and Lu and x is 0 through 0.55) and single crystal of a compound obtained by substituting part of the lead of the above single crystal by at least an element selected from Ba, Sr, Ca and La such as $Pb\{(Zn1/3Nb2/3)0.91Ti0.09\}O3$ (to be referred to as PZNT91/9 hereinafter).

Preferably, the piezoelectric members of the piezoelectric vibrators for wave transmission are made of a lead relaxa-titanate type monocrystalline piezoelectric material generally having a low frequency constant while the piezoelectric members of the piezoelectric vibrators for wave reception are made of a PZT type piezoelectric ceramic material. This is because, when this probe 10 is used for THI, for instance, it is desirable that the resonance frequency of the piezoelectric vibrators for wave transmission is about twice as high as the center frequency of the operating frequency band of the piezoelectric vibrators for wave reception.

While the resonance frequency can be controlled by controlling the thickness of the piezoelectric vibrators, the piezoelectric vibrators for wave transmission and those for wave reception preferably have the same thickness, from the viewpoint of manufacturing them. Specifically, the piezoelectric members preferably have a thickness between about 200 and about 600 $\mu$m.

The electrodes 114a, 115a are made of an electrode-forming material mainly containing Au, Ag, Pd and/or Sn.

For forming the electrodes, a foundation metal layer of Ti or Cr is formed to a thickness of 0.02 to 1.0 $\mu$m typically by sputtering and then a layer of a metal material mainly containing Au, Ag, Pd and/or Sn or an alloy thereof is formed thereon, if necessary, with an insulating material partly added thereto to a thickness of 1 to 10 $\mu$m by sputtering or some other appropriate technique. The electrodes may alternatively be formed from electrically conductive paste obtained by mixing micro-powder of metal and low melting point glass and using a technique of screen printing, dipping or flame-coating without relying on sputtering.

A predetermined voltage is then applied to the electrodes 114a, 115a arranged on the opposite surfaces of the piezoelectric member 113a to polarize the piezoelectric member and produce a piezoelectric vibrator.

Figure 12:
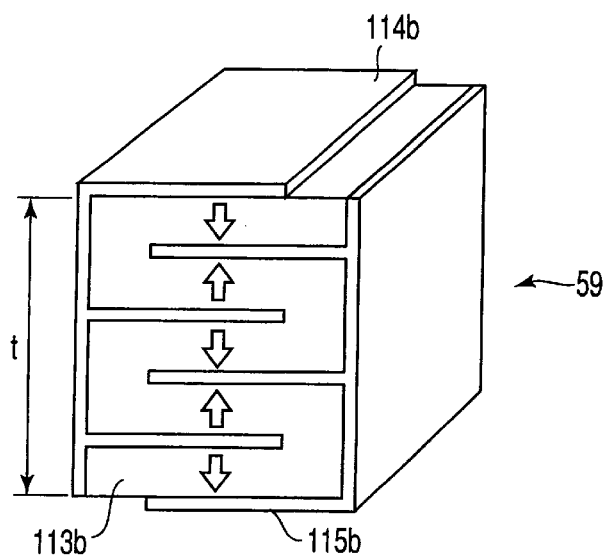
FIG. 12 is a schematic perspective view of a piezoelectric vibrator obtained by modifying that of FIG. 11.

FIG. 12 is a schematic perspective view of a piezoelectric vibrator obtained by modifying that of FIG. 11.

The layer-built piezoelectric vibrator 59 as shown in FIG. 12 is formed by sequentially laying a first electrode 114b and a second electrode 115b and piezoelectric members 113b are formed in a number of layers between the electrodes. The first electrode 114b and the second electrode 115b are connected at the lateral sides of the piezoelectric vibrator.

The piezoelectric vibrator can be produced by applying a predetermined voltage between the first electrode 114b and the second electrode 115b to polarize adjacently located piezoelectric members in opposite directions, as indicated by the arrows in FIG. 12.

The center frequency of the resonance frequency band of the obtained piezoelectric vibrator is defined by the total thickness 1 of the piezoelectric members 113b. Therefore, if the piezoelectric vibrator of FIG. 12 and the piezoelectric vibrator of FIG. 11 comprising a single layer of a piezoelectric member shown in FIG. 11 are made of the same material and have the same dimensions, they substantially show the same effective thickness t and the same center frequency.

A layer-built piezoelectric vibrator 59 as shown in FIG. 12 provides an advantage that a low voltage can be used to drive the piezoelectric vibrator because the distance separating the electrodes is reduced. Particularly, the use of such layer-built piezoelectric vibrators as those for wave transmission is effective when they are used to form an ultrasonic diagnosis apparatus for THI.

Another advantage of such layer-built piezoelectric vibrators 59 is that they can be used to provide a large capacity. Generally, in a two-dimensional array probe comprising piezoelectric vibrators, the ultrasonic wave receiving surface of each piezoelectric vibrator will be as small as 0.1 mm$^2$ or less. Then, each piezoelectric vibrator will have a small electrical capacitance, producing an impedance which is too large for operating frequency band of 2 to 5 MHz that is normally used for drive signals. Then, it will be difficult to make the impedance match that of the connection cable to be used with it. On the other hand, the impedance of piezoelectric vibrator 59 as shown in FIG. 12 can be matched to that of the connection cable to be used with it to consequently reduce the signal noise level, because the thickness of each of the piezoelectric members can be reduced to raise the electrical capacity of the piezoelectric vibrator as a result of layering the electrodes. Therefore, it may be wise if a large number of layers of piezoelectric vibrators are used as vibrators 11a for wave transmission and a small number of layers of piezoelectric vibrators are used as vibrators 11b for wave reception. For example, the piezoelectric vibrators 11a for wave transmission may be made to have 7 to 10 layers, while the piezoelectric vibrators 11b for wave reception are made to have 1 to 3 layers.

Now, a method of manufacturing a layer-built piezoelectric vibrator will be described by referring to FIGS. 13A through 13I. Note that in each of FIGS. 13A, 13B, 13D, 13E, 13F and 13G, the upper half shows a plan view of the layer-built piezoelectric vibrator in the illustrated manufacturing step and the lower half shows a lateral view of the layer-built piezoelectric vibrator in the same step.

Figure 13A:
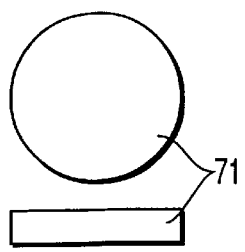
FIGS. 13A through 13I are schematic views of layer-built piezoelectric vibrators in different manufacturing steps.
Figure 13B:
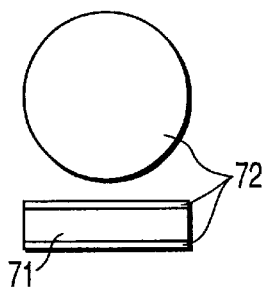

Firstly, a plurality of (disk-shaped) piezoelectric members 71 that are PZT ceramic plates or lead relaxa-titanate type single crystal plates, each having a thickness of 50 to 100 $\mu$m and a diameter of 20 to 30 mm are prepared as shown in FIG. 13A and electrodes 72 are formed on the opposite surfaces of each of the piezoelectric members 71 as shown in FIG. 13B.

When forming each of the electrodes 72, firstly a foundation metallic layer of Ti or Cr is formed to a thickness of 0.02 to 1.0 $\mu$m, typically by sputtering, and then a layer of a metallic material mainly containing Au, Ag, Pd and/or Sn or an alloy thereof is formed thereon, if necessary, with an insulating material partly added thereto to a thickness of 1 to 10 $\mu$m by sputtering or some other appropriate technique. The electrodes may alternatively be formed from electrically conductive paste obtained by mixing micro-powder of metal and low melting point glass and using a technique of screen printing, dipping or flame-coating without relying on sputtering.

Figure 13C:
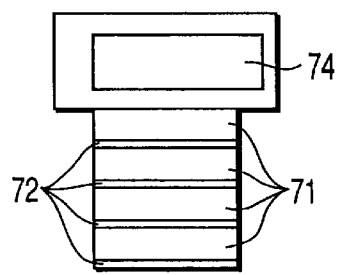

Then, as shown in FIG. 13C, the piezoelectric members 71 now carrying the respective electrodes 72 are laid one on the other to bring each electrode into contact with one of the electrodes of another piezoelectric member and an appropriate weight 74 is put on top before the piezoelectric members 71 are heated to 300 to 800° C. for about 10 minutes. The heat treatment temperature varies depending on the electrode material. For example, the electrodes can be bonded together at a temperature as low as 300° C. if they are made of 80 Au/20Sn or 95 Sn/5Ag. However, a sufficient bonding strength cannot be obtained until the electrodes are heated to about 800° C. if they are made of 70 Pd/30 Ag.

Figure 13D:
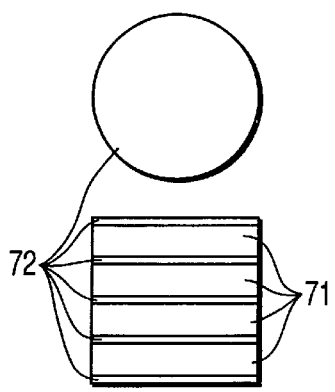
Figure 13E:
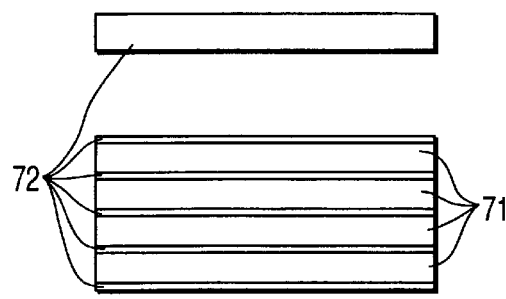

The obtained multilayered body as shown in FIG. 13D is sliced to a width of about 0.2 to 0.5 mm to produce a plurality of strip-shaped multilayered bodies as shown in FIG. 13E.

Figure 13F:
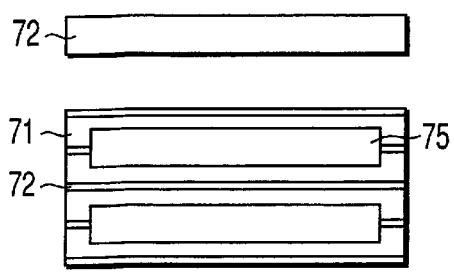
Figure 13G:
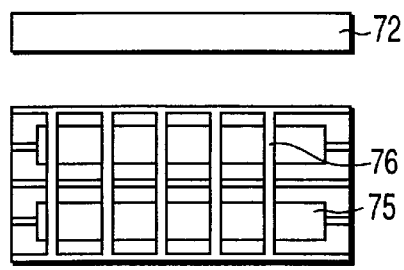

Thereafter, every other electrode 72 is covered by an insulating glass material 75 at the lateral sides of each strip-shaped multilayered body as shown in FIG. 13F and an external electrode 76 is formed on the glass material 75 on the lateral sides of the multilayered body in a manner as shown in FIG. 13G.

Note that, while the second and the fourth electrodes 72 are covered by the glass material 75 and the first, the third and the fifth electrodes are electrically connected on the lateral side shown in FIG. 13G, the first, the third and the fifth electrodes are covered by the glass material 55 and the second and the fourth electrodes are electrically connected on the other lateral side.

The multilayered body of FIG. 13G is made to show piezoelectric characteristics by cooling it from 200° C. to 20° C. while applying a voltage (electric field) between 0.1 and 2 kV/mm to a pair of opposite electrodes of the multilayered body, to polarize the piezoelectric members 71.

Figure 13H:
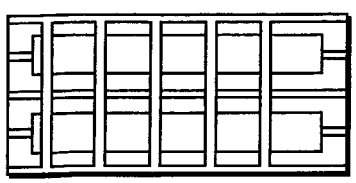
Figure 13I:
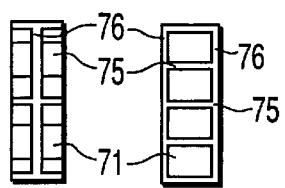

Then, the multilayered body is cut to pieces 0.2 to 0.5 mm wide as shown in FIG. 13H to produce piezoelectric vibrators, each having a profile as shown in FIG. 13I (FIG. 13I shows a lateral view and a plan view of a piezoelectric vibrator Now, a method of manufacturing an ultrasonic probe 10 will be described below.

(1) Preparation of a Vibrator for Wave Transmission

Solid solution type single crystal of PZNT91/9 is used for piezoelectric members. A (001) plate of the single crystal is sliced to produce a 20 mm×20 mm pieces, which are then polished until they show a thickness of 100 $\mu$m. Electrically conductive paste obtained by adding glass paste to Au/Pt is applied to the opposite surfaces of each of the single crystal plate and baked at 650° C. to form a pair of electrodes. Five piezoelectric members carrying electrodes are laid one on the other and heated at 700° C. for 10 minutes to bond them together under pressure.

The obtained multilayered body is cut to pieces 0.25 mm wide. Low melting point glass is formed on the surface of the first, the third and the fifth electrodes exposed at one of the lateral sides produced by the slicing and also on the surface of the second, the fourth and the sixth electrodes exposed at the other lateral sides, at a temperature of 550° C., for insulation. Thereafter, an external electrode is formed on each of the lateral sides by sputtering.

The multilayered body carrying external electrodes is cut at intervals of 0.25 mm to produce piezoelectric vibrators having dimensions of 0.25 mm (length) 0.25 mm (width)× 0.5 mm (height).

Thereafter, a voltage of 0.3 kV/mm (about 30V) is applied to the external electrodes at 180° C. to polarize the piezoelectric members. According to an observation of the inventors of the present invention, each of the obtained piezoelectric members shows an electric capacity of about 250 pF, a center frequency of an operating frequency band of about 2.0 MHz and a coupling coefficient k33 of about 80%.

(2) Preparation of Vibrator for Wave Reception

PZT ceramic is used for the piezoelectric members of a piezoelectric vibrator for wave reception.

An standard method of forming layers of green sheets is used. Firstly, 20 to 100 $\mu$m thick green sheets of a PZT type material are formed by means of a sheet molding machine. A predetermined pattern is printed on the surface of each green sheet by using electrode paste mainly contain Pt, Pd and/or Ag. The sheets are accurately aligned and laid one on the other. Subsequently, the multilayered structure is cut to produce individual vibrators, which are then degreased and baked. Thereafter, external electrodes are attached to the vibrators as in the case of the vibrators for wave transmission to produce finished vibrators having dimensions of 0.25 mm (length)×0.25 mm (width)×0.5 mm (height).

Thereafter, a voltage of 2 kV/mm is applied to the external electrodes of each piezoelectric vibrator at 80° C. to polarize the piezoelectric members.

According to an observation of the inventors of the present invention, each of the obtained layer-built piezoelectric members shows an electric capacity of about 200 pF, a center frequency of an operating frequency band of about 3.0 MHz and a coupling coefficient k33 of about 65%.

The prepared vibrators for wave transmission and those for wave reception are then evaluated for characteristics to obtain a required number of good ones.

While different materials are used for piezoelectric members in order to produce piezoelectric vibrators with different resonance frequencies in this embodiment, a technique of differentiating the thickness of piezoelectric members, that of differentiating the ultrasonic wave receiving surface and the direction of polarization or that of using 2-cycle vibrators as piezoelectric vibrators for wave reception may alternatively be used for the purpose of the invention.

However, it should be noted that the use of piezoelectric vibrators having an identical thickness is preferable in view of the need of arranging piezoelectric vibrators in such a way that their ultrasonic wave receiving surfaces are substantially flush with each other.

When differentiating piezoelectric members, piezoelectric members that can make the center frequency of the operating frequency band of the vibrators for receiving ultrasonic waves is preferably 1.5 to 2 times higher than the center frequency of the operation frequency band of the vibrators for transmitting ultrasonic waves.

When differentiating the ultrasonic wave receiving surface and the direction of polarization of piezoelectric members, the vibrators for wave transmission may be arranged in such a way that the direction of polarization agrees with that of the ultrasonic wave receiving surfaces, while the vibrators for wave reception may be arranged in such a way that the direction of polarization is perpendicular to that of the ultrasonic wave receiving surfaces so that the piezoelectric vibrators of one of the two different types may emit ultrasonic waves generated in the k33 vibration mode from their ultrasonic wave receiving surfaces and the piezoelectric vibrators of the other type may emit ultrasonic waves generated in the k31 vibration mode from their ultrasonic wave receiving surfaces.

When using 2-cycle vibrators as piezoelectric vibrators for wave reception, single layer or layer-built piezoelectric vibrators as shown in FIG. 11 or 12, whichever are appropriate, are used as vibrators for wave transmission while 2-cycle vibrators having a cross section as shown in FIG. 14A or 14B are used as vibrators for wave reception.

FIGS. 14A and 14B show 2-cycle vibrators. The piezoelectric vibrator of FIG. 14A comprises a polarized piezoelectric member 91 and an un-polarized material 92 showing no piezoelectric characteristics along with a first electrode 93 and a second electrode 94 formed respectively on opposite surfaces of the piezoelectric member 91. On the other hand, the piezoelectric vibrator of FIG. 14B comprises a first electrode 95, a first piezoelectric member 96, a second electrode 97, a second piezoelectric member 98 and a third electrode 99 that are laid sequentially in the above order, of which the first piezoelectric member 96 and the second piezoelectric member 98 are polarized in opposite directions.

Such 2-cycle vibrators have two frequency bands including frequency f1 of piezoelectric vibrators for wave transmission and higher harmonics of the second degree f2 (f2=f1×2). Therefore, they can effectively detect not only higher harmonics but also the basic wave. Additionally, they can be used for forming harmonic images such as THI and tomographic images that are conventionally obtained by using the basic wave with a good S/N.

(3) Preparation of Two-Dimensional Array Ultrasonic Probe

The method of manufacturing a two-dimensional array ultrasonic probe comprising at least piezoelectric vibrators of one of the two types with different resonance frequencies as described in (1) and (2) above will be discussed below by way of three examples.

1ST EXAMPLE

In the first embodiment, a sparse array type two-dimensional array probe designed not to a use all the piezoelectric vibrators arranged in the form of matrix but only part thereof is prepared so that different vibrators are used for wave transmission and reception. This example clearly shows the characteristic aspects of the invention.

In this first example, k33 type layer-built piezoelectric vibrators are used. K33 refers to the electromechanical coupling coefficient and means that the direction of voltage application agrees with the direction of vibration and the layer-built piezoelectric vibrators vibrate in a longitudinal vibration mode.

FIG. 16 shows layer-built piezoelectric vibrators 30 for transmitting an ultrasonic wave to the object of examination, layer-built piezoelectric vibrators 32 for receiving the wave reflected by the object of examination and unused vibrators 34 (dummy vibrators) that are not used for transmitting nor receiving an ultrasonic wave. Both the layer-built piezoelectric vibrators 30 for ultrasonic wave transmission and the layer-built piezoelectric vibrators 32 for ultrasonic wave reception are piezoelectric members that utilizes the k33 vibration mode where the direction of main vibration (the direction of the thickness) agrees with the direction of laying piezoelectric vibrators. Note that the number of layers of the layer-built piezoelectric vibrators 30 for wave transmission is relatively large whereas that of the layer-built piezoelectric vibrators 32 for wave reception is relatively small or only one. This is because the vibrators for wave transmission are adapted to transmit an ultrasonic wave with a low voltage and a high acoustic pressure, whereas the vibrators for wave reception are so designed that their impedance is suitable for a wave receiving circuit and can improve the efficiency of transmitting the received signal.

The layer-built piezoelectric vibrators 30 for wave transmission used in this example will be described in greater detail below.

Figure 17A:
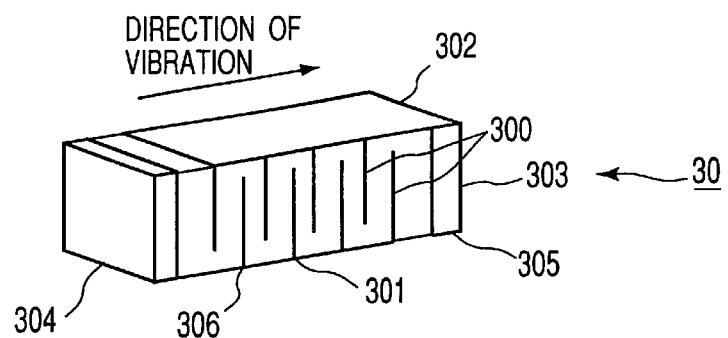
FIG. 17A is a schematic perspective view of a k33 type layer-built piezoelectric vibrator 30.

FIG. 17A is a schematic perspective view of one of the layer-built piezoelectric vibrators 30 for wave transmission.

In FIG. 17A, the layer-built piezoelectric vibrator 30 for eave transmission comprises internal electrodes 300 arranged between the layers of the vibrator, electrode link sections 301, 302 formed on the lateral surfaces of the vibrator and connected to the internal electrodes 300, a signal electrode 304 and a grounding electrode 303. On the lateral surface (facing the printed circuit board) of the layer-built piezoelectric vibrator 30 for wave transmission, the lateral sides of the signal electrode 304 and the grounding electrode 303 are used as connecting sections with the signal line 161 and the grounding line 165.

Now, the process of mounting the layer-built piezoelectric vibrators 30 for wave transmission, the layer-built piezoelectric vibrators 32 for wave reception and the dummy vibrators 34 on a printed circuit board 16 of the second type will be described.

Firstly, as shown in FIG. 16, the piezoelectric layer-built piezoelectric vibrators are arranged in such a way that the side of the signal electrode 304 faces the corresponding signal connection pad 163 of the printed circuit board 16 and the side of the grounding electrode 303 faces the corresponding ground connection pad 162. In FIG. 16, the piezoelectric vibrators of the three different types are arranged non-cyclically.

Then, each printed circuit board 16 of the second type is put in a solder reflow furnace to melt the solder paste of the connection pads and the solder layer to connect the grounding electrodes 303 and the signal electrodes 304 with the respective connection pads 162, 163. As a result, the printed circuit board 16 of the second type is mounted with the layer-built piezoelectric vibrators 30 for wave transmission, the layer-built piezoelectric vibrators 32 for wave reception and the dummy vibrators 34.

The steps following the above step of preparing printed circuit boards 16 of the second type mounted with different vibrators are the same as those described earlier for the first embodiment and hence will not be described any further.

While dummy vibrators are mounted as unused vibrators 34, they may be replaced by layer-built piezoelectric vibrators for wave transmission or wave reception so long as they are actually not used.

The above described two-dimensional array ultrasonic probe 10 uses layer-built piezoelectric members for the vibrators and the piezoelectric vibrators for wave transmission and those for wave reception are differentiated by the number of layers. Then, leads are drawn from the vibrators mounted on the printed circuit board 16 of the second type. With this arrangement, leads can be drawn with ease as in the case of using single layer vibrators although the vibrators are actually made of layer-built piezoelectric members having a complex and delicate structure. Additionally, since the vibrators are mounted on a one by one basis, vibrators for wave transmission and those for wave reception can be made to show different sets of characteristics. Differently stated, vibrators having a large number of layers are used for wave transmission, whereas those having a relatively small number of layers (or a single layer) are used for wave reception so that they may be adapted to the electric circuit of the reception system. Therefore, this arrangement of transducers can operate with a high efficiency for transmitting/receiving ultrasonic waves.

Totally different vibrators are used for the vibrators for wave transmission and those for wave reception in this example (by using individual elements). However, the idea of this example can also be applied to an arrangement where some of the vibrators for wave transmission and/or some of the vibrators for wave reception are used for both wave transmission and wave reception.

2ND EXAMPLE

In this second example, k31 type layer-built piezoelectric vibrators are used. K31 refers to a mode of vibration along the longitudinal direction of piezoelectric vibrators where the direction of vibrators and the direction of the voltage application are perpendicular to each other.

Figure 17B:
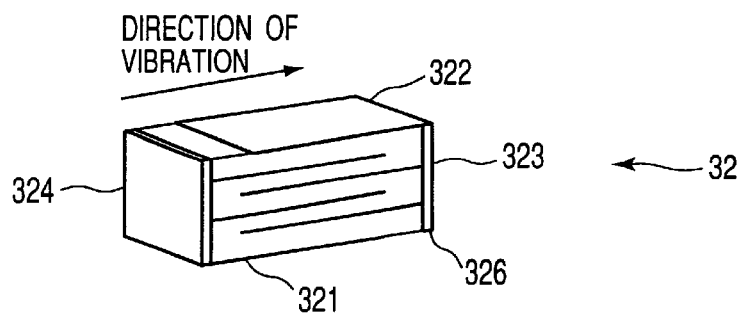
FIG. 17B is a schematic perspective view of a k31 type layer-built piezoelectric vibrator and FIG. 17C is a perspective view of a printed circuit board, illustrating a method of mounting a k31 type layer-built piezoelectric vibrator thereon.
Figure 17C:
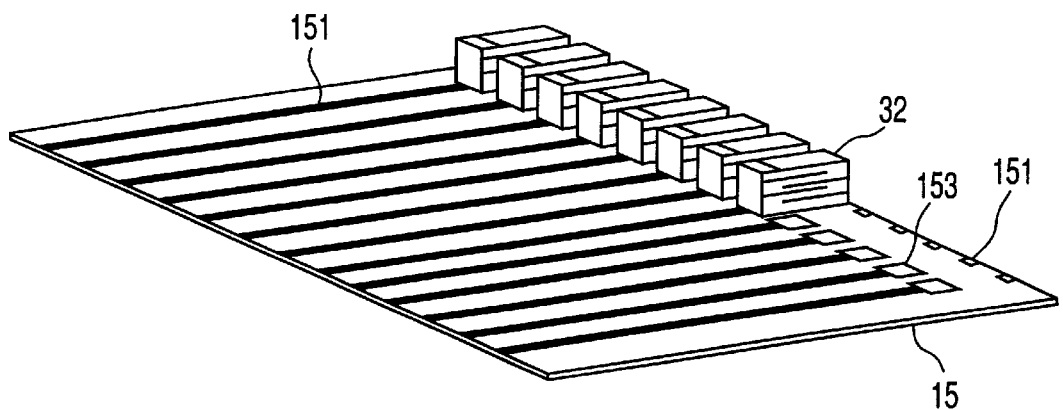

FIG. 17B shows a k31 type layer-built piezoelectric vibrator 32. The ultrasonic irradiation surface and the layering direction of the piezoelectric vibrator are orthogonal relative to each other in a k31 type layer-built piezoelectric vibrator 32. Therefore, the side of the signal electrode 321 of the vibrator 32 is arranged to face the printed circuit board 15 and that of the grounding electrode 322 is oppositely arranged. Additionally, a link electrode 323 is arranged on the ultrasonic wave irradiation side to link the grounding electrode 322 and the corresponding pad on the printed circuit board 16, while another link electrode 324 is arranged on the opposite side to link the signal electrode 321 and the corresponding pad on the printed circuit board 16. A connecting section 326 is arranged along the edge of the link electrode 323 to be located close to the printed circuit board.

The k31 type layer-built piezoelectric vibrator 32 is mounted on the printed circuit board 15 in such a way that the signal electrode 321 and the connecting section 326 are located respectively vis-a-vis the signal connection pad 153 and the ground connection pad 151 of the printed circuit board. The mounting process, the subsequent manufacturing processes and the configuration of the finished product are the same as their counterparts of the first embodiment, described earlier.

The above arrangement of this second example provides the advantages as those of the first embodiment. Additionally, it is possible to provide the advantages of the first example by altering the number of layers of each k31 type layer-built piezoelectric vibrator. Note that a two-dimensional array probe comprising k31 type layer-built piezoelectric vibrators can be manufactured more easily than a two-dimensional array probe comprising k33 type layer-built piezoelectric vibrators so that the yield of manufacturing two-dimensional array transducers can be raised by using k31 type layer-built piezoelectric vibrators.

3RD EXAMPLE

In this example, both k31 type layer-built piezoelectric vibrators and k33 type layer-built piezoelectric vibrators are used. More specifically, k31 type layer-built piezoelectric vibrators are used as piezoelectric vibrators for wave transmission and k33 type layer-built piezoelectric vibrators are used as piezoelectric vibrators for wave reception to realize a mixed type ultrasonic probe. A sparse array type probe can be realized by additionally using dummy vibrators to arrange piezoelectric vibrators of three different types in an intermingled fashion. Then, preferably, the piezoelectric vibrators for wave reception are made to show a center frequency of an operating frequency band 1.5 to 2 times higher than that of the piezoelectric vibrators for wave transmission. The process of mounting piezoelectric vibrators on printed circuit boards 15 and the subsequent manufacturing processes are the same as their counterparts of the first and second examples.

The piezoelectric vibrators for wave transmission of the ultrasonic probe of this example emits an ultrasonic wave of about 2.0 MHz. Since the center frequency of the piezoelectric vibrators for wave reception adapted to receive the higher harmonics of the second degree, or the echo centered at the frequency of 4.0 MHz, is as high as 3.0 MHz, the probe can receive the higher harmonics of the second degree with an enhanced level of sensitivity and hence it is possible to suppress the voltage to be applied to the piezoelectric vibrators for wave transmission.

Finally, the advantages of the first and second embodiments of two-dimensional array ultrasonic probe according to the invention will summarily discussed below by comparing them with conventional two-dimensional array ultrasonic probes.

Firstly, when manufacturing a two-dimensional array ultrasonic probe by a known method, a plate-shaped piezoelectric vibrator is typically placed on a substrate having m×n electrode leads and mechanically and electrically connected thereto. Then, the plate-shaped piezoelectric vibrator is cut into m×n pieces to produce a two-dimensional array. If m and n are greater than 50 and the pitch of arrangement of the final piezoelectric vibrators is as small as less than 0.5 mm, more than 2,000 ch wires have to be drawn from an area of 2 cm square to produce so may channels. Such an operation may require the circuit board to have a multilayer structure and the use of micro-pattern forming techniques to consequently raise the cost of the circuit board and hence the manufacturing cost. Furthermore, it is highly difficult to divide a plate-shaped piezoelectric vibrator into more than 2,000 pieces and inevitably resulting in defective vibrators and other problems.

On the contrary, the first or second embodiment of two-dimensional array ultrasonic probe according to the invention is produced by arranging printed circuit boards, each carrying a row of piezoelectric vibrators, in parallel with each other. Signal wires are lead from the respective piezoelectric vibrators by way of the signal lines formed on each printed circuit board. Therefore, wires can be led out far more easily compared to the conventional method. As a result, it is possible to manufacture, at low cost, a two-dimensional array ultrasonic probe with a high sensitivity and low inter-vibrator cross talk to realize a high manufacturing efficiency. Additionally, since printed circuit boards, each carrying an array of piezoelectric vibrators, are arranged in parallel with each other, unlike conventional methods of arranging a plurality of flexible printed circuit boards, each carrying a single piezoelectric vibrator, it is possible to reduce the number of manufacturing steps and raise the productivity.

Secondly, the micro-vibrators formed by way of a conventional two-dimensional array ultrasonic probe are accompanied by the problem of an increased vibrator impedance. Since the ultrasonic vibrators are made of a piezoelectric material, each vibrator that operates like a capacitor is forced to show a large impedance when its dimensions and hence the surface area thereof are reduced. A high impedance means a large transmission loss that arises when the voltage generated in the vibrator by the received ultrasonic wave is transmitted to the downstream electric circuits resulting in a poor sensitivity. Techniques of using layer-built piezoelectric vibrators to reduce the impedance have been proposed. However, with a conventional two-dimensional array ultrasonic probe, such a technique requires the use of a layer-built piezoelectric structure to be incorporated into each vibrator that is to be produced from a large piezoelectric plate and hence electrode patterns and through holes have to be prepared at a high density and accuracy, which is practically impossible.

On the contrary, with the second embodiment of a two-dimensional array ultrasonic probe according to the invention, layer-built piezoelectric members that are processed into the form of a large number of vibrators are arranged in a row at a predetermined pitch on a printed circuit board where signal lines for leading out signal wires are already formed and a plurality of printed circuit boards, each carrying a row of piezoelectric vibrators, are arranged in parallel with each other. Signal wires are led from each piezoelectric vibrator by way of the signal lines formed on the printed circuit board for that piezoelectric vibrator. Therefore, wires can be led out far more easily than in conventional methods. As a result, it is possible to manufacture a small and highly sensitive two-dimensional array ultrasonic probe at low cost to realize a high productivity even when layer-built piezoelectric members are used for piezoelectric vibrators.

Now, the method of manufacturing a two-dimensional array ultrasonic probe according to the invention will be compared with a conventional method with which a plate-shaped piezoelectric vibrator is typically on a substrate having m×n electrode leads for mechanical and electric connection and then the plate-shaped piezoelectric vibrator is cut into m×n pieces to produce a two-dimensional array. While signal wires can be led out from individual piezoelectric vibrators with such a method, it is difficult to draw out wires individually from the common electrode (grounding side) that is arranged opposite to the piezoelectric vibrators. Additionally, in the conventional method, the common electrode has to be commonly connected to the vibrators formed by dividing the piezoelectric plate and separate lines have to be led out therefrom. Consequently, the grounding line of each vibrator is located remotely from the signal line of the vibrator, which increase cross talk among the signal lines.

On the contrary, with the first and second embodiments of two-dimensional array ultrasonic probe according to the invention, grounding wires are led out from the respective piezoelectric vibrators by way of the grounding lines formed on the printed circuit boards carrying piezoelectric vibrators thereon. Therefore, grounding wires can be led out more far easily than in the conventional method and cross talk can be effectively suppressed among the signal lines.

Next, the method of manufacturing a two-dimensional array ultrasonic probe according to the invention will be compared with a conventional method with which array probes of a single row are prepared and bonded together to produce a two-dimensional array probe structure. This method does not require the use of highly sophisticated printed circuit boards and it is relatively easy to draw grounding wires from individual vibrators and use layer-built piezoelectric members. However, this method is accompanied by a problem that it is difficult to down-size the vibrators. Since the two-dimensional array structure produced by this conventional method is similar to the structure of a one-dimensional array ultrasonic probe and grounding electrode plates and flexible printed circuit boards are arranged between vibrators in the direction of laying one-dimensional arrays, the grounding plates and the FPC boards have a configuration of being bent along corresponding ends of vibrators so that it is difficult to provide a sufficient gap between any two vibrators. Additionally, when array probes of a single row are prepared and bonded together to produce a two-dimensional array probe structure, the vibrators are arranged neatly in rows and columns with a high level of accuracy even for the height of the surfaces. Such a level of accuracy cannot be achieved when bent grounding plates and FPC boards are used.

On the contrary, with the first and second embodiments of the two-dimensional array ultrasonic probe according to the invention, layer-built piezoelectric members that are processed in advance to show the profile of vibrators are arranged in a single row at a predetermined pitch on a printed circuit board provided with signal lines for leading out signal wires. Then, a number of such printed circuit boards are arranged in parallel with each other. Signal wires are led out from respective piezoelectric vibrators by way of signal lines formed on the printed circuit board. Therefore, it is not necessary to provide separate grounding plates for grounding wires and FPC boards for signal wires. Furthermore, the FPC boards do not need to be bent. As a result, it is possible to manufacture a highly sensitive two-dimensional array ultrasonic probe with minimal inter-vibrator cross talk at low cost.

While the present invention is described by way of preferred embodiments and examples, it is by no means limited thereto and it will be obvious to those who are skilled in the art that they can be modified and altered in various different ways without departing from the scope of the invention. Any such modifications and alternations are also within the scope of the present invention.

Thus, according to the invention, there are provided a highly sensitive two-dimensional array ultrasonic probe with minimal inter-vibrator cross talk, a method of manufacturing such a probe with ease at low cost and an ultrasonic diagnosis apparatus comprising such a probe.

Additionally, to accommodate THI technology according to the invention, it is possible to provide an ultrasonic probe to be suitably used for low power consumption high sensitivity ultrasonic diagnosis or ultrasonic diagnosis using THI technology, a method of manufacturing such an ultrasonic probe with ease and an ultrasonic diagnosis apparatus.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An ultrasonic probe comprising:
   a plurality of substrates each of which includes first base-electrodes arranged at predetermined intervals and second base-electrodes arranged corresponding to the first base-electrodes;
   a plurality of layer-built vibrators each of which includes first internal electrodes, second internal electrodes arranged corresponding to the first internal electrodes, piezoelectric vibrators formed between the first internal electrodes and the second internal electrodes, a first external electrode connected to the first internal electrodes, and a second external electrode connected to the second internal electrodes, a respective first external electrode connected to one of the first base-electrodes and a respective second external electrode connected to one of the second base-electrodes so that the layer-built vibrators are arranged in an array arrangement; and
   a holder which holds said plurality of substrates at regular intervals in such a manner to arrange the plurality of layer-built vibrators in a matrix arrangement.

2. The ultrasonic probe according to claim 1, wherein the plurality of layer-built vibrators comprise wave-transmission vibrators and wave-reception vibrators, and
   each of the wave-transmission vibrators includes the first internal electrodes, the second internal electrodes and piezoelectric vibrators greater in number than those of each of the layer-built vibrators for each of the wave-reception vibrators.

3. The ultrasonic probe according to claim 1, wherein the plurality of substrates comprise flexible printed circuit boards.

4. The ultrasonic probe according to claim 1, wherein the first external electrodes and the second external electrodes are arranged on a first side of a respective layer-built vibrator along a direction of ultrasonic wave-transmission and reception.

5. The ultrasonic probe according to claim 1, wherein the second base-electrodes are connected to the ground.

6. The ultrasonic probe according to claim 5, wherein the second base-electrodes are lead out to a second side different from the first side of the substrate.

7. The ultrasonic probe according to claim 1, wherein the holder includes a backing member having grooves arranged at predetermined regular intervals, and the plurality of substrates are held by being inserted into respective grooves.

8. The ultrasonic probe according to claim 1, wherein the plurality of layer-built vibrators are mounted on the substrates with a layered direction held in agreement with direction of ultrasonic wave-transmission and reception.

9. The ultrasonic probe according to claim 1, wherein the plurality of layer-built vibrators are mounted on the plurality of substrates with a layered direction held substantially perpendicularly relative to a direction of ultrasonic wave-transmission and reception.

10. The ultrasonic probe according to claim 1, wherein the plurality of layer-built vibrators comprise at least a plurality of first vibrators to transmit a first ultrasonic wave within a first frequency band and at least a plurality of second vibrators to receive a reflected wave within a second frequency band, and a center frequency of the second frequency band is higher than a center frequency of the first frequency band.

11. The ultrasonic probe according to claim 10, wherein external dimensions of which of the first vibrators are substantially the same as those of each of the second vibrators, and a material of the first vibrators is different from a material of the second vibrators.

12. The ultrasonic probe according to claim 10, wherein a piezoelectric vibrator of the first vibrator includes a single crystal of lead relaxa-titanate, and a piezoelectric vibrator of the second vibrator includes a PZT type piezoelectric ceramic material.

13. The ultrasonic probe according to claim 10, wherein each of the first vibrators vibrates is in a same direction as a direction of application of the voltage, and each of the second vibrators vibrates in a direction perpendicular to a direction of application of the voltage.

14. The ultrasonic probe according to claim 10, wherein the external electrodes of the first vibrators are formed on a first side of a respective layer-built vibrator in either a parallel or perpendicular direction to an ultrasonic wave-transmission and reception, and the external electrodes of the second vibrators are formed on a second side in either a parallel or perpendicular direction to the first side.

15. An ultrasonic probe comprising:

a plurality of first layer-built vibrators each of which includes first internal electrodes, second internal electrodes arranged corresponding to the first internal electrodes, first piezoelectric vibrators formed between the first internal electrodes and the second internal electrodes, a first external electrode connected to the first internal electrodes, and a second external electrode connected to the second internal electrodes and each of which generates an ultrasound wave in a first frequency band;

a plurality of second layer-built vibrators each of which includes third internal electrodes, fourth internal electrodes arranged corresponding to the third internal electrodes, second piezoelectric vibrators formed between the third internal electrodes and the fourth internal electrodes, a third external electrode connected to the first internal electrodes, and a fourth external electrode connected to the second internal electrodes and each of which generates an ultrasound wave in a second frequency band;

a plurality of substrates each of which includes first base-electrodes arranged at predetermined intervals and connected to the first or third external electrode, and includes second base-electrodes arranged corresponding to the first base-electrodes and connected to the second or fourth external electrode; and a holder which holds the plurality of substrates at regular intervals in such a manner to arrange the plurality of layer-built vibrators in a matrix arrangement.

16. The ultrasonic probe according to claim 15, wherein external dimensions of each of the first layer-built vibrators are substantially the same as those of each of the second layer-built vibrators, and a respective first piezoelectric vibrator is different from a respective second piezoelectric vibrator.

17. The ultrasonic probe according to claim 15, wherein a respective first piezoelectric vibrator includes a single crystal of lead relaxa-titanate, and a respective second piezoelectric vibrator includes a PZT type piezoelectric ceramic material.

18. The ultrasonic probe according to claim 15, wherein each of the first layer-built vibrators vibrates is in a same direction as a direction of application of the voltage, and each of the second layer-built vibrators vibrates in a direction perpendicular to a direction of application of the voltage.

19. The ultrasonic probe according to claim 15, wherein the first and second external electrodes are formed on a first side of a respective first layer-built vibrator in either a parallel or perpendicular direction of an ultrasonic wave-transmission and reception, and the third and fourth external electrodes of the second vibrators are formed on a second side in either a parallel or perpendicular direction to the first side.

20. A method of manufacturing an ultrasonic probe comprising:

forming electrodes on first and second surfaces of each of piezoelectric plates;

laminating the piezoelectric plates and connecting the electrodes together, thereby forming a first laminated member in which the piezoelectric plates and the electrodes are alternately stacked;

forming a plurality of first external electrodes and a plurality of second external electrodes on a first side surface which is along a lamination direction, at predetermined pitches, the first external electrodes being used for connecting even-numbered ones of the electrodes, and the second external electrodes being used for connecting odd-numbered ones of the electrodes;

subjecting the piezoelectric plates to polarization processing;

cutting the first lamination member into pieces along planes that are between positions of the pitches, thereby obtaining a plurality of layer-built vibrators;

arranging the layer-built vibrators in an array along one side of a plurality of substrates in such a manner that the first external electrodes are electrically connected to first base-electrodes and the second external electrodes are electrically connected to second base-electrodes, the first base-electrodes and the second base-electrodes being arranged at a predetermined pitch on the substrate; and forming an ultrasonic wave transmission-reception surface by holding the plurality of substrates at regular intervals in such a manner as to arrange the plurality of layer-built vibrators in a matrix arrangement.

21. The method of manufacturing an ultrasonic probe according to claim 20, wherein the plurality of layer-built vibrators include layer-built vibrators for wave transmission and layer-built vibrators for wave reception, each having layers smaller in number than those of each of the layer-built vibrators for wave transmission, arranged in an intermixed way.

22. The method of manufacturing an ultrasonic probe according to claim 20, wherein the ultrasonic transmission-reception surface is formed by inserting the plurality of substrates into respective grooves formed at predetermined regular intervals in a backing member.

23. The method of manufacturing an ultrasonic probe according to claim 20, wherein the ultrasonic transmission-reception surface is formed by bonding the plurality of substrates to respective backing members and laying the substrates bonded to the respective backing members one on the other.

24. The method of manufacturing an ultrasonic probe according to claim 20, wherein the plurality of substrates comprise flexible printed circuit boards.

* * * * *